United States Patent
Kevlahan et al.

(10) Patent No.: US 9,790,467 B2
(45) Date of Patent: Oct. 17, 2017

(54) METHODS AND COMPOSITIONS FOR ACTIVATION OR EXPANSION OF T LYMPHOCYTES

(71) Applicant: QT Holdings Corp, Beverly, MA (US)

(72) Inventors: Sean H. Kevlahan, North Reading, MA (US); Andrew Ball, Georgetown, MA (US); Guokui Qin, Somerville, MA (US); Steven B. Wells, Allston, MA (US); Nithya Jothi Jesuraj, Woburn, MA (US)

(73) Assignee: QT Holdings Corp, Beverly, MA (US)

( * ) Notice: Subject to any disclaimer, the term of this patent is extended or adjusted under 35 U.S.C. 154(b) by 0 days.

(21) Appl. No.: 15/228,905

(22) Filed: Aug. 4, 2016

(65) Prior Publication Data

US 2017/0081636 A1 Mar. 23, 2017

Related U.S. Application Data

(60) Provisional application No. 62/354,416, filed on Jun. 24, 2016, provisional application No. 62/221,743, filed on Sep. 22, 2015.

(51) Int. Cl.
*C07K 16/00* (2006.01)
*C12N 5/0783* (2010.01)
*C07K 16/28* (2006.01)

(52) U.S. Cl.
CPC ........ *C12N 5/0636* (2013.01); *C07K 16/2809* (2013.01); *C07K 16/2818* (2013.01); *C07K 2317/31* (2013.01)

(58) Field of Classification Search
None
See application file for complete search history.

(56) References Cited

U.S. PATENT DOCUMENTS

| | | | |
|---|---|---|---|
| 6,352,694 B1 | 3/2002 | June et al. | |
| 6,534,055 B1 | 3/2003 | June et al. | |
| 6,642,363 B1 | 11/2003 | Mooney et al. | |
| 7,204,139 B2 | 4/2007 | Takayama | |
| 7,214,245 B1 | 5/2007 | Marcolongo et al. | |
| 7,592,431 B2 | 9/2009 | Har-Noy | |
| 2001/0051374 A1 | 12/2001 | McLaughlin-Taylor et al. | |
| 2003/0235908 A1 | 12/2003 | Berenson et al. | |
| 2006/0094060 A1 | 5/2006 | Jarhede et al. | |
| 2006/0121012 A1 | 6/2006 | Kutryk et al. | |
| 2006/0141045 A1 | 6/2006 | Bhatt et al. | |
| 2009/0041825 A1 | 2/2009 | Kotov et al. | |
| 2010/0144902 A1 | 6/2010 | Shu | |
| 2010/0261270 A1 | 10/2010 | Peeters et al. | |
| 2011/0144286 A1 | 6/2011 | Wu | |
| 2012/0270209 A1 | 10/2012 | Shah et al. | |
| 2013/0017264 A1 | 1/2013 | Khandare et al. | |
| 2013/0315880 A1 | 11/2013 | Frank | |
| 2014/0057280 A1 | 2/2014 | Murthy et al. | |
| 2014/0154703 A1 | 6/2014 | Skelley et al. | |
| 2015/0030619 A1 | 1/2015 | Milone et al. | |
| 2015/0118318 A1 | 4/2015 | Fahmy et al. | |

FOREIGN PATENT DOCUMENTS

| | | | |
|---|---|---|---|
| EP | 2034009 A2 | 3/2009 | |
| EP | 2177236 A1 | 4/2010 | |
| WO | WO-03/040235 A1 | 5/2003 | |
| WO | WO 2006020580 | * | 2/2006 |
| WO | WO 2006096746 | * | 9/2006 |
| WO | WO-2010/124227 A2 | 10/2010 | |
| WO | WO-2011/078990 A1 | 6/2011 | |
| WO | WO 2011078990 | * | 6/2011 |
| WO | WO-2012/042467 A2 | 4/2012 | |
| WO | WO 2012148684 | * | 4/2012 |
| WO | WO-2012/106658 A1 | 8/2012 | |
| WO | WO 2013188786 | * | 6/2013 |
| WO | WO 2015148512 | * | 3/2015 |
| WO | WO-2015/148512 A1 | 10/2015 | |
| WO | WO-2015/168379 A2 | 11/2015 | |

OTHER PUBLICATIONS

Williams et al., "Human T lymphocytes and hematopoietic cell lines express CD24-associated carbohydrate epitopes in the absence of CD24 mRNA or protein," Blood. 88(8): 3048-55 (1996).
International Search Report and Written Opinion for International Patent Application No. PCT/US2016/053103, dated Dec. 7, 2016 (14 pages).
Casati et al., "Clinical-scale selection and viral transduction of human naïve and central memory CD8+ T cells for adoptive cell therapy of cancer patients," Cancer Immunol Immunother. 62(10): 1563-73 (2013).
Flynn et al., "Stem memory T cells (TSCM)—their role in cancer and HIV immunotherapies," Clin Transl Immunology. 3(7): e20 (2014) (7 pages).
Levine et al., "Antiviral effect and ex vivo CD4+ T cell proliferation in HIV-positive patients as a result of CD28 costimulation," Science. 272(5270): 1939-43 (1996).
Levine et al., "Effects of CD28 costimulation on long-term proliferation of CD4+ T cells in the absence of exogenous feeder cells," J Immunol. 159(12): 5921-30 (1997).
O'Connor et al., "Substrate rigidity regulates human T cell activation and proliferation," J Immunol. 189(3): 1330-9 (2012) (11 pages).
Rasmussen et al., "Ex vivo expansion protocol for human tumor specific T cells for adoptive T cell therapy," J Immunol Methods. 355(1-2): 52-60 (2010).
Sunshine et al., "Particle shape dependence of CD8+ T cell activation by artificial antigen presenting cells," available in PMC Jan. 1, 2015, published in final edited form as: Biomaterials. 35(1): 269-77 (2014) (17 pages).
Trickett et al., "T cell stimulation and expansion using anti-CD3/CD28 beads," J Immunol Methods. 275(1-2):251-5 (2003).

(Continued)

*Primary Examiner* — Michail Belyavskyi
(74) *Attorney, Agent, or Firm* — Clark & Elbing LLP

(57) ABSTRACT

The invention features a complex that binds to, stimulates, and expands a desired T cell population and facilitates separation of the target population from a sample. The complex can be gently dissociated from the binding unit after separating the desired T cell population, representing a safe and efficient approach for processing T cells for clinical use. Invention also provides methods of using such complexes as part of adoptive T cell therapy systems.

26 Claims, 29 Drawing Sheets

(56) References Cited

OTHER PUBLICATIONS

Tumeh et al., "The impact of ex vivo clinical grade activation protocols on human T cell phenotype and function for the generation of genetically modified cells for adoptive cell transfer therapy," available in PMC Oct. 1, 2011, published in final edited form as: J Immunother. 33(8):759-68 (2010) (17 pages).

Turtle et al., "CD19 CAR-T cells of defined CD4+:CD8+ composition in adult B cell ALL patients," J Clin Invest. 126(6): 2123-38 (2016).

Fatin-Rouge et al., "Removal of some divalent cations from water by membrane-filtration assisted with alginate," Water Res. 40(6):1303-1309 (2006).

Hatch et al., "Engineered Alginate Hydrogels for Effective Microfluidic Capture and Release of Endothelial Progenitor Cells from Whole Blood," available in PMC Apr. 5, 2012, published in final edited form as: Langmuir. 27(7):4257-64 (2011) (16 pages).

Mahou et al., "Novel Alginate-Poly(ethylene glycol) Hydrogel for Immobilization and Delivery: Synthesis and Physical Properties Assessment," XVIIth Int. Conference on Bioencapsulation, Sep. 24-26, Groningen, Netherlands. pp. 1-4, Poster P63 (2009) (2 pages).

Plouffe et al., "Controlled capture and release of cardiac fibroblasts using peptide-functionalized alginate gels in microfluidic channels," Lab Chip. 9(11):1507-10 (2009).

Yamaguchi et al., "Polysaccharide-poly(ethylene glycol) star copolymer as a scaffold for the production of bioactive hydrogels," Biomacromolecules 6(4):1921-30 (2005).

Verbeke et al., "Multicomponent Injectable Hydrogels for Antigen-Specific Tolerogenic Immune Modulation," Adv Healthc Mater. (2017) (15 pages).

* cited by examiner

A

B

A

B

METHODS AND COMPOSITIONS FOR ACTIVATION OR EXPANSION OF T LYMPHOCYTES

FIELD OF THE INVENTION

The invention is generally directed to the fields of T cell activation, cell culture, and bioprocessing. More specifically, the invention is directed toward improved protocols for manufacturing large numbers of viable engineered T lymphocytes for clinical immunotherapy applications.

BACKGROUND

T lymphocytes isolated from whole blood are utilized in a wide variety of in vitro, in vivo, and clinical research and therapeutic applications. Examples include studies of immune response, T cell receptor signaling, cytokine release and gene expression profiling. Perhaps most significantly, isolation and subsequent ex vivo engineering of T lymphocytes for subsequent transplantation into clinical patients is showing tremendous promise as a novel cancer therapy. The main approaches to this are engineering of T cells to express either chimeric antigen receptors (CAR) or T cell receptors (TCR). In both approaches, T cells are isolated from whole blood, activated and expanded ex vivo, and subsequently infused into human subjects.

Although both polyclonal and antigen-specific T cells can be readily isolated from whole blood, their numbers are limited. Accordingly, protocols that activate and promote ex vivo expansion of T cells are widely used. Such ex vivo manipulations, however, can potentially reduce T cell viability, proliferation, and survival after infusion. Thus, the choice of methods used for T cell activation has important implications for clinical efficacy.

It is well-established that, in vivo, activation of T cells is dependent on two signals; engagement of the T cell receptor with antigen (signal 1) and ligation of a costimulatory molecule (signal 2). Both are required for an effective immune response. Ex vivo, T cell activation is most commonly induced by exposing the T cells to antibodies directed against the T cell surface markers CD3 and CD28 to engage the T cell receptor and deliver a costimulatory signal simultaneously.

There are significant disadvantages of conventional ex-vivo T cell activation protocols, which use magnetic beads, resulting from the presence of residual magnetic beads attached to the cells. These may negatively affect both function and viability. Pre-clinical clinical applications require cells are that are free from contaminating particles, while retaining high viablilty. For example, June et al. (Pilot study of redirected autologous T cells engineered to contain humanized anti-CD19 in patients with relapsed or refractory CD19+ leukemia and lymphoma previously treated with cell therapy (2015) *ClinicalTrials.gov*) specified final product release criteria in the IND included the specifications that the number of anti-CD3/CD28-coated paramagnetic beads should not exceed 100 per $3 \times 10^6$ cells and that cell viability should be greater than 70%. However, minimizing the number of beads represents a formidable obstacle in the clinical translation of such therapies, as most antibody-coated magnetic-bead based products lack the ability to readily release bound cells from capture molecules in a manner that does not alter the viability and phenotype of the isolated cells.

Given the significant interest in, and rapid expansion of, T cell engineering-based cancer therapies, there is a significant need for improved T cell activation and harvesting methods that overcome the above limitations of existing approaches, particularly for downstream clinical applications. Specifically, there is a substantial need for technologies to enable ex-vivo cell expansion protocols to meet clinical specifications, to consistently and reproducibly activate T cells, to preserve cell viability and function, and to be applicable to different cell sources and activating agents.

SUMMARY OF THE INVENTION

We have developed a unique hydrogel that is biocompatible, functionalized with T cell activating ligands such as antibodies, and can be dissolved rapidly simply by switching to a buffer containing a chelating agent. Together, these properties provide a unique technology that eliminates retained cell tagging agents, such as magnetic beads, from isolated cell populations. Among its many benefits, the dissolution process does not affect cell viability as other coating chemistries do.

In one aspect, the invention features a complex including a binding unit, i.e., hydrogel, and a separation unit, e.g., magnetic beads, in which the binding unit includes a polymeric moiety and binds a cell surface component of a lymphocyte, and the separation unit dissociates from the binding unit upon exposure of the polymeric moiety to an ion chelator. In some embodiments, the separation unit is entrapped within the polymeric moiety. In a preferred embodiment, the polymeric moiety comprises a polymer that changes from a solid matrix into a solution or suspension in response to decrease in cationic concentration (e.g., $Li^+$, $Mg^{2+}$, $Ca^{2+}$, $Sr^{2+}$, $Ba^{2+}$, $Zn^{2+}$, $Cu^{2+}$, or $Al^{3+}$) caused by the presence of an ion chelator (e.g., EDTA, EGTA, sodium citrate, BAPTA, crown ether, cryptand, phenanthroline sulfonate, dipyridyl sulfonate, dioxane, DME, diglyme, or triglyme). In some embodiments, the elastic modulus of the polymeric moiety is between 100 pascals (Pa) and 100,000,000 Pa (e.g., from 100 Pa to 1,000 Pa, from 1,000 Pa to 10,000 Pa, between 10,000 Pa to 100,000 Pa, between 100,000 Pa and 1,000,000 Pa, 1,000,000 Pa and 10,000,000 Pa, or 10,000,000 Pa and 100,000,000 Pa, e.g., less than 1,000,000 Pa, less than 900,000 Pa, less than 800,000 Pa, less than 700,000 Pa, less than 600,000 Pa, less than 500,000 Pa, less than 400,000 Pa, less than 300,000 Pa, less than 200,000 Pa, less than 100,000 Pa, less than 50,000 Pa, or less than 10,000 Pa). In some embodiments, the polymer is a hydrogel such as alginic acid or an alginic acid-polyethylene glycol (PEG) copolymer, e.g., having a median viscosity of between about 10 and 100 kDa (e.g. about 10, 20, 30, 40, 50, 60, 70, 80, 90, or 100 kDa).

In certain embodiments, the binding unit includes a magnetic material, such as iron. In some embodiments, the magnetic material is part of a nanoparticle or a microparticle, e.g., which can have a polymeric coating.

In one aspect, the complex of the invention has at least one dimension of between about 50 nm and about 50 μm (e.g. 50 nm, 100 nm, 200 nm, 300 nm, 400 nm, 500 nm, 600 nm, 700 nm, 800 nm, 900 nm, 1 μm, 2 μm, 3 μm, 4 μm, 5 μm, 10 μm, 20 μm, 30 μm, 40 μm, or 50 μm). In some aspects, the complex is spherical. In some aspects, the diameter is between about 1 and 20 μm (e.g., 1 μm, 2 μm, 3 μm, 4 μm, 5 μm, 10 μm, 20 μm).

In some embodiments, the binding moiety is conjugated to the polymeric moiety after the separation unit is entrapped within the polymeric moiety. In other embodiments, the binding moiety is conjugated to the polymeric moiety before the separation unit is entrapped within the polymeric moiety.

In some embodiments, the binding moiety is covalently attached to an alginic acid domain, e.g., of an alginic acid-PEG copolymer (e.g., covalently attached through a carboxylate group of the alginic acid).

In one aspect, the invention features a complex having a signal 1 stimulus. In some aspects, the complex has both a signal 1 stimulus and a signal 2 stimulus. In some embodiments, the molar ratio of the signal 1 stimulus to the signal 2 stimulus is between about 1:100 and about 100:1 (e.g., about 1:100, about 1:80, about 1:50, about 1:25, about 1:10, about 1:5, about 1:4, about 1:3, about 1:2, about 1:1, about 2:1, about 3:1, about 4:1, about 5:1, about 10:1, about 25:1, about 50:1, about 80:1, or about 100:1). In some embodiments, the molar ratio of the signal 1 stimulus to the signal 2 stimulus is between about 1:10 and about 10:1. In some embodiments, the molar ratio of the signal 1 stimulus to the signal 2 stimulus is between about 1:2 and about 2:1. In some embodiments, the molar ratio of the signal 1 stimulus and the signal 2 stimulus is greater than 1:1, and in other embodiments, the molar ratio of the signal 1 stimulus and the signal 2 stimulus is less than 1:1.

In one embodiment, the binding moiety has an antigen-specific signal 1 stimulus. In another embodiment, the signal 1 stimulus is antigen-nonspecific. In some aspects, the binding moiety includes an antibody or antigen-binding fragment thereof. In these aspects, the antibody or antigen binding fragment thereof is a monoclonal antibody or antigen-binding fragment thereof, a Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv') 2) molecule, a domain antibody, a diabody, a triabody, an affibody, a domain antibody, a SMIP, a nanobody, a Fv fragment, a Fab fragment, a F(ab') 2 molecule, or a tandem scFv (taFv) fragment.

In one embodiment, the binding moiety binds one or more human antigens.

In one aspect, the invention features a complex with binding moiety made up of one or more antibodies or antigen-binding fragments thereof selected from the group of anti-CD2, anti-CD3, anti-CD27, anti-CD28, anti-CD46, anti-CD137, or antigen binding fragments thereof. In one aspect, the signal 1 stimulus is anti-CD3. In another aspect, the signal 2 stimulus is anti-CD28. In another aspect, the complex includes both a signal 1 stimulus that is anti-CD3 and a signal 2 stimulus is anti-CD28.

In some aspects, the binding moiety is covalently attached to the polymeric moiety. In some aspects, the complex has density of at least 1 binding moiety per square μm of surface area (e.g., at least 1, 2, 3, 4, 5, 6, 7, 8, 9, 10, 15, 20, 30, 40, 50, 60, 70, 80, 90, 100, or more binding moieties per square μm of surface area.

In another aspect, the invention features a method of activating a population of T cells involving; first, contacting a starting population of T cells with complexes each having binding unit and a separation unit, in which the binding unit binds a surface component of a T cell, and in which the contacting induces a metabolic change in the starting population of T cells; second, treating the complex with an ion chelator, which dissociates the separation unit from the T cells; and lastly, isolating a resulting population of T cells from the separation unit. In one embodiment, the ion chelator chelates a cation (e.g., $Li^+$, $Mg^{2+}$, $Ca^{2+}$, $Sr^{2+}$, $Ba^{2+}$, $Zn^{2+}$, $Cu^{2+}$, $Al^{3+}$). In one embodiment, the chelator includes EDTA, EGTA, sodium citrate, BAPTA, crown ether, cryptand, phenanthroline sulfonate, dipyridyl sulfonate, dioxane, DME, diglyme, or triglyme.

In one embodiment, the separation unit is magnetic, and the isolation is performed using a magnet.

In one embodiment, the population of T cells is antigen-specific. In a different embodiment, the population of T cells is antigen-nonspecific. In one embodiment, the population of T cells is tumor-specific. In another embodiment, the population of T cells includes CD4 T cells. In another embodiment, the population of T cells includes CD8 T cells. The resulting population of T cells may have a number or percentage of CD8 T cells that is greater than the number or percentage of CD8 T cells of a starting population (e.g., 10% more, 20% more, 30% more, 40% more, 50% more, 75% more, or greater).

Additionally or alternatively, the resulting population of T cells may have a number or percentage of CD8 T cells that is greater than the number or percentage of CD4 T cells in the resulting population. In another embodiment, the population of T cells includes NK T cells. In another embodiment, the population of T cells includes regulatory T cells.

In some embodiments, the resulting population of cells has at least 2% naïve T cells (e.g., at least 3%, at least 4%, at least 5%, at least 6%, at least 7%, at least 8%, at least 9%, at least 10%, or more, e.g., about 5%, about 10%, about 15%, or more). In some embodiments, the resulting population of cells has at greater number or percentage of naïve T cells relative to cells expanded by magnetic beads without a hydrogel coating (e.g., Dynabeads, e.g., 10% more, 20% more, 50% more, 100% more, or greater, e.g., 2-fold more, 3-fold more, 4-fold more, 5-fold more, 10-fold more, or greater). Additionally or alternatively, the resulting population of cells may have a greater number or percentage of central memory T cells than the starting population (e.g., 10% more, 20% more, 30%, more, 40% more, 50% more, 75% more, 100% more, 150% more, 200% more, 300% more, 400% more, 500% more, 1,000% more, 5,000% more, 10,000% more, or greater). In some embodiments, the naïve T cells are $CD45RA^+$ cells, $CD45RA^+CD62L^+$ cells, or $CD45RA^+CCR7^+$ cells. In other embodiments, the naïve T cells secrete lower quantities of IL-4 and/or IFN-γ than a reference population of cells (e.g., wherein the reference population is the starting population, a central memory cell population, an effector memory population, or an activated population).

In one embodiment, the population of T cells is isolated from a subject. In a different embodiment, the population of T cells is derived from a cell line. In one aspect, the starting population of T cells comprises a genetic modification, such as that resulting from a chimeric antigen receptor (CAR) modification.

In one aspect, the metabolic change induced in the T cells by contacting them with the complexes includes a biochemical or a morphological change. This change may be a greater frequency of cell division, a change in cytokine secretion profile (e.g., of IL-4 and/or IFN-γ), an increase in median cell diameter, a change surface molecule expression profile, or a change in cellular motility.

In another aspect, the method includes seeding the starting population of T cells at a concentration of between about $0.2 \times 10^6$ and $10 \times 10^6$ cells/ml (e.g., $0.2 \times 10^6$, $0.4 \times 10^6$, $0.6 \times 10^6$, $0.8 \times 10^6$, $1.0 \times 10^6$, $2.0 \times 10^6$, $3.0 \times 10^6$, $4.0 \times 10^6$, $5.0 \times 10^6$, or $10 \times 10^6$ cells/ml). In yet another aspect, the method includes seeding the starting population of T cells and the complexes at a ratio between about 1:100 and about 100:1 (e.g., about 1:100, about 1:80, about 1:50, about 1:25, about 1:10, about 1:5, about 1:4, about 1:3, about 1:2, about 1:1, about 2:1, about 3:1, about 4:1, about 5:1, about 10:1, about 25:1, about 50:1, about 80:1, or about 100:1).

In another embodiment, the method includes a step of treating the complex with an ion chelator multiple times over the course of the T cell expansion process. In another embodiment, the method further includes contacting the population of T cells with a plurality of complexes multiple times over the course of T cell expansion process. In one aspect, the isolation of the resulting population of T cells from the separation unit is performed after a predetermined length of time, or alternatively, it is performed after the resulting population of T cells acquires a desired phenotype.

In some embodiments of any of the preceding methods, cell culture media can be supplemented with ions, such as $Ca^{2+}$, through addition of salts, e.g., $CaCl_2$. Ions can be present at any physiologically suitable concentration (e.g., 1.0 nM-100 mM, e.g., 1.0 µM to 10 mM, e.g., 0.1 mM, 0.2 mM, 0.5 mM, 1.0 mM, 2 mM, 3 mM, 4 mM, 5 mM, 6 mM, 7 mM, 8 mM, 9 mM, or 10 mM).

In some embodiments, T cells expanded by any of the compositions or methods of the present invention express CD8 and CD4, e.g., at a ratio of between 1:10 and 10:1, e.g., at a ratio of 1:10, 1:8, 1:5, 1:2, 1:1, 2:1, 5:1, 8:1, or 10:1. In particular embodiments, the number of T cells expressing CD8 is greater than the number of T cells expressing CD4 in the expanded population. Complexes and methods of the invention can induce an expanded T cell culture having a greater proportion of $CD8^+$ cells than a population expanded by conventional means (e.g., anti-CD3/CD28 coated beads).

BRIEF DESCRIPTION OF THE DRAWINGS

FIG. 6A shows the expression of CD3 versus the uptake of propidium iodide (PI) as a marker of cell death after a twelve-day expansion protocol. FIG. 6B shows the relative expression of CD8 versus CD4 after a twelve-day expansion protocol.

FIG. 7A shows the expression of CD3 versus the uptake of propidium iodide (PI) as a marker of cell death after a twelve-day expansion protocol. FIG. 7B shows the relative expression of CD8 versus CD4 after a twelve-day expansion protocol.

FIG. 9A shows expression of CD8 versus CD4. FIG. 9B shows expression of CD45RA versus CD3. FIG. 9C shows expression of CD45RO versus CD3. FIG. 9D shows expression of CD62L versus CD45RA. FIG. 9E shows expression of CCR7 versus CD45RA.

FIG. 10A shows expression of CD8 versus CD4. FIG. 10B shows expression of CD45RA versus CD3. FIG. 10C shows expression of CD45RO versus CD3. FIG. 10D shows expression of CD62L versus CD45RA. FIG. 10E shows expression of CCR7 versus CD45RA.

FIG. 11A shows expression of CD8 versus CD4. FIG. 11B shows expression of CD45RA versus CD3. FIG. 11C shows expression of CD45RO versus CD3. FIG. 11D shows expression of CD62L versus CD45RA. FIG. 11E shows expression of CCR7 versus CD45RA.

DETAILED DESCRIPTION OF THE INVENTION

Figure 1:
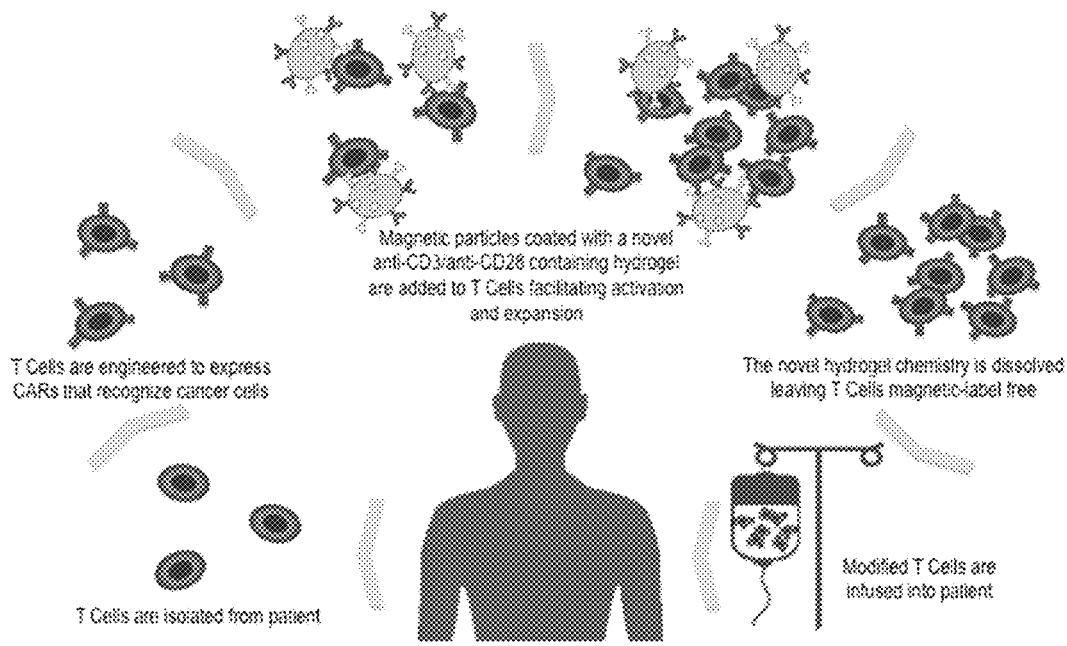
FIG. 1: Workflow for the manufacture of CAR T cells using anti-CD3/anti-CD28 complexes for T Cell activation and expansion. Post expansion, the complex is dissolved away leaving T Cells magnetic-label free increasing viability and reducing negative host response.

The invention provides a complex that binds to, stimulates, and expands a desired T cell population and facilitates separation of the target population from a sample. The complex can be gently dissociated from the binding unit after separating the desired T cell population, representing a safe and efficient approach for processing T cells for clinical use. The invention also provides methods of using such complexes as part of adoptive T cell therapy systems.

Binding Unit

The invention features a complex having a binding unit and a separation unit. The binding unit includes a binding moiety that binds a component on a T cell surface. The binding moiety is linked to a polymeric moiety that includes a cation-sensitive hydrogel. The binding moiety and the polymeric moiety, together, form the binding unit.

T Cell Binding Moieties

In one aspect, the invention features a binding moiety that can bind to a surface component of a T cell. Preferably, this binding event can lead to signal transduction within the T cell, resulting in activation and/or proliferation of the target cell. Several T cell surface molecules are known to have these downstream effects. In general, any ligand that induces clustering of the T cell receptor (signal 1) is able to stimulate that T cell to proliferate and, depending on a secondary signal (signal 2), differentiate towards a particular functional phenotype. Preferably, the signal 1 agent of the present invention is anti-CD3, and the signal 2 agent of the present invention is anti-CD28. Other examples of signal 1 stimuli include MHC-I or MHC-II, and agonists of various other T cell receptor components known in the art. Other examples of signal 2 stimuli include antigen-presenting cell surface molecules that are agonists of co-stimulatory molecules (e.g., CD80, CD86, CD40, ICOSL, CD70, OX40L, 4-1BBL, GITRL, LIGHT, TIM3, TIM4, ICAM1, or LFA3), antibodies toward T cell costimulatory surface molecules other than CD28 (e.g., CD40L, ICOS, CD27, OX40, 4-1 BB, GITR, HVEM, Galectin 9, TIM-1, LFA-1, and CD2), antigen-presenting cell surface molecules that are agonists of co-inhibitory molecules (e.g., CD80, CD86, PD-L1, PD-L2, B7-H3, B7-H4, HVEM, ILT3, or ILT4), and antibodies against co-inhibitory molecules (e.g., CDTL-4, PD-1, BTLA, or CD160). Signal 2 stimulation has been shown to affect multiple aspects of T cell activation. It lowers the concentration of anti-CD3 required to induce a proliferative response in cultures and enhances cytokine production to direct T cell differentiation pathways. Importantly, costimulation helps activate cytolytic potential of CD8 T cells. Other molecules, including but not limited to CD2 and CD137, can be targeted in activation protocols used to activate and expand various T cell populations, such naïve and memory T cells, T helper cells, regulatory T cells, Natural Killer T cells and Cytotoxic T Lymphocytes from mouse and human samples. Additional examples of antibodies, ligands, and other agents useful as signal 1 and signal 2 stimuli for use in the present invention are described in WO2003/024989.

Antigen-Specific T Cell Engagement

In one aspect of the invention, a binding unit may bind a T cell receptor in an antigen-specific manner analogous to the binding that occurs between the T cell receptor and a peptide-MHC on an antigen presenting cell. Synthetic methods to engage a T cell in an antigen specific manner (i.e., in the absence of a natural antigen presenting cell) include MHC class I and MHC class II multimers (e.g., dimers, tetramers, and dextramers). Illustrative examples are described in U.S. Pat. No. 7,202,349 and U.S. 2009/0061478. Multimerization of MHC-peptide complexes functions to enhance avidity of interaction between peptide-MHC and T cells, which increases the potency of signal 1 transduction. Another means to achieve multivalent presentation of antigen-specific T cell receptor ligands is by tethering the ligands to a surface of a complex. Affinity, in contrast to avidity, describes the strength of binding of each individual molecule. The affinity of peptide-MHC for a T cell receptor can vary dramatically and dictates the downstream effect of signal 1 stimuli, as discussed below. Antigens, and peptides thereof, for use in the present invention include, but are not limited to melanoma antigen recognized by T cells (MART-1), melanoma GP100, the breast cancer antigen, Her-2/Neu, and mucin antigens. Other relevant antigens and sources thereof are described, for example, in U.S. Pat. No. 8,637,307.

Effects of the Degree of T Cell Binding

The relative degree of signal 1 and signal 2 binding can influence TCR signal transduction and lead to varying downstream phenotypic effects. For example, high affinity with low avidity signal 1, in the absence of signal 2, primes a naïve CD4 T cell to turn on Foxp3 expression and differentiate toward a regulatory phenotype (Gottschalk et al., *Journal of Experimental Medicine* 207 (2010): 1701).

Alternatively, in response to a high avidity signal 1 stimulus without sufficient signal 2 stimulus, a naïve T cell may be more likely to undergo exhaustion, leading to functional anergy (see Ferris et al., *J Immunol August* 15; 193 (2014): 1525-1530). Either of these effects would be undesireable in the context of cancer adoptive immunotherapy but may be helpful in when priming regulatory T cells for autoimmune treatment. Thus, the relative contribution of signal 1 and signal 2 can be rationally modulated, depending on the application, by exposing the functionalized complex to a desired ratio of binding moieties.

The binding moieties may be coupled to the same surface or to separate surfaces. In a preferred embodiment, a signal 1 stimulus and a signal 2 stimulus are immobilized on the surface at a 1:1 ratio. In certain aspects of the present invention, a signal 1 stimulus and a signal 2 stimulus are immobilized on the surface at a ratio of other than 1:1 (e.g., between about 1:100 and about 100:1, between about 1:10 and 10:1, between about 1:2 and 2:1). In other aspects, the ratio of signal 1 stimulus to signal 2 stimulus immobilized on the surface is greater than 1:1, or less than 1:1.

The effect of relative strength of signaling between signal 1 and signal 2 also depends on the activation state of the target T cell. For instance, naïve T cells react differently to T cell receptor stimulation and costimulation than antigen-experienced T cells. A skilled artisan would appreciate this effect when selecting a configuration of binding units of the present invention, especially in cases of chronic infection or aberrant immune tolerance, and configure the binding unit accordingly.

Size and Shape of the Complex

The complex may be formed into any shape compatible with contacting the surface of a T cell. For this reason, however, it is often preferable for a complex to have a high surface area to volume ratio to maximize the available binding surface. Artificial antigen presenting cell platforms having different sizes and shapes have been evaluated for various functional benefits (see Fadel et al., *Nano Letters* 8 (2008): 2070-2076; Sunshine et al., Biomaterials 35 (2014): 269-277). The shape of the structure may be any suitable shape, such as elongated like a wire, tubular, i.e., having a lumen, planar, or spherical. An immune synapse can range in size from less than 50 nm to about 20 µm. Preferably, the complex of the present invention is spherical, and the size is between 50 nm and 20 µm. For example, the complex can be the size of antigen presenting cells, such as dendritic cells or macrophage, which range from about 10-20 µm and 10-20 µm, respectively. Alternatively, the complex can include a larger matrix, such as a porous scaffold, which can be mechanically exposed, e.g. dipped, into a suspension of cells. Methods for synthesizing such scaffolds, including by using alginate, are known in the art.

Polymeric Moiety

The binding unit of the present invention can be linked to the separation unit by conjugation to a polymeric moiety. Preferably, this conjugation occurs through a covalent reaction.

Polymeric moieties useful in the present invention include hydrogels that can be dissolved by changing the ionic composition of their environment. Hydrogels of the invention are formed from alginic acid conjugated to a polyalkylene oxide, e.g., PEG, as generally described in WO 2012/106658. Conjugation of alginic acid to multifunctional PEG confers greater mechanical strength compared with that achieved solely by ionic crosslinking of alginate. Thus, the mechanical properties (e.g. stiffness) can be modulated by increasing the number of functional groups on each PEG molecule. PEG is useful as part of the present invention because of its superior hydrophilic properties, which prevent protein adsorption to the complex of the present invention. Adsorption of serum proteins onto the complex can result in aberrant signaling pathways in adjacent cells, such as those caused by Fc receptor engagement. The hydrophilic properties of PEG are also functional to maintain a high diffusivity within the complex interior, such that ionic chelators can rapidly access the complex interior to quickly sequester rigidity-maintaining cations. Thus, incorporation of branched PEG molecules within the hydrogel ensures a rapid dissolution of the hydrogel structure upon exposure to appropriate stimuli. Alternatively, any other biocompatible hydrophilic polymer (e.g. polyvinyl pyrrolidone, polyvinyl alcohol, and copolymers thereof) can be substituted (see, e.g., U.S. Pat. No. 7,214,245).

A polymeric moiety of the invention can have one or more mechanical properties (e.g., elastic modulus, Young's modulus, compression modulus, or stiffness) suitable for T cell expansion. For example, the mechanical properties of the polymeric moiety can be tailored to be suitable to allow an population of T cells (e.g., a population containing expanded T cells) to retain one or more characteristics of a naïve phenotype (e.g., as described in the Methods section) after contacting a complex of the invention. In some cases, the elastic modulus of the polymeric moiety is between 100 pascals (Pa) and 100,000,000 Pa (e.g., from 100 Pa to 1,000 Pa, from 1,000 Pa to 10,000 Pa, between 10,000 Pa to 100,000 Pa, between 100,000 Pa and 1,000,000 Pa, 1,000,000 Pa and 10,000,000 Pa, or 10,000,000 Pa and 100,000,000 Pa, e.g., less than 1,000,000 Pa, less than 900,000 Pa, less than 800,000 Pa, less than 700,000 Pa, less than 600,000 Pa, less than 500,000 Pa, less than 400,000 Pa, less than 300,000 Pa, less than 200,000 Pa, less than 100,000 Pa, less than 50,000 Pa, or less than 10,000 Pa).

A reference to alginic acid is also a reference to a salt form, e.g., sodium alginate, unless otherwise noted. Suitable alginic acid is 20 kDa medium viscosity alginic acid. Alginic acid can be present in the polymer moiety in a percentage (e.g., a weight-by-volume percentage) between 0.01 and 10% (e.g., from 0.1% to 0.15%, from 0.15% to 0.2%, from 0.2% to 0.3%, from 0.3% to 0.4%, from 0.4% to 0.5%, from 0.5% to 0.6%, from 0.6% to 0.7%, from 0.7% to 0.8%, from 0.8% to 0.9%, from 0.9% to 1.0%, from 1.0% to 2%, from 2% to 5%, from 5% to 7.5%, or from 7.5% to 10%, e.g., about 0.2%, 0.25%, 0.3%, 0.35%, 0.4%, 0.45%, 0.5%, 0.6%, 0.7%, 0.75%, 0.8%, 0.9%, 1.0%, 1.5%, 2.0%, 2.5%, 3%, 3.5%, 4%, 4.5%, 5%, or 10%). The alginic acid content of the polymeric moiety will influence the stiffness of the polymeric moiety according to known principles (e.g., cation content of the polymeric moiety). The stiffness of alginate polymeric moieties can be varied while maintaining a constant or near-constant density according to known methods.

Polyalkylene oxides, e.g., PEG and polypropylene oxide, are known in the art. Linear or branched, e.g., 4-arm or 8-arm, polyalkylene oxides, e.g., PEG, may be employed. The polyalkylene oxide, e.g., PEG, preferably has a molecular weight between 10 kDa and 20 kDa. An exemplary ratio of polyalkylene oxide, e.g., PEG, to alginic acid is 1:2 by weight.

Alginic acid naturally possesses multiple carboxyl groups that provide convenient groups for conjugation to polyalkylene oxide, e.g., PEG, and/or binding moieties. The polyalkylene oxide, e.g., PEG, and binding moiety will naturally possess or be modified to possess an appropriate group to conjugate to a carboxyl group. Suitable groups include amine groups, which are often found in binding moieties that include amino acids or can be introduced into binding moieties and polyalkylene oxides, e.g., PEG. For example, amine-terminated polyalkylene oxide, e.g., PEG, can be employed. In other embodiments, a linker may be use to conjugate appropriate groups on the polyalkylene oxide, e.g., PEG, or binding moiety to carboxyl groups on the alginic acid. In the hydrogel, a single polyalkylene oxide, e.g., PEG, may be conjugated to one or more alginic acid molecules. When a polyalkylene oxide binds to more than one alginic acid, the number of such crosslinks in the composition may or may not be sufficient to form a gel. The binding moiety can bind to either the alginic acid directly or to a polyalkylene oxide, e.g., PEG, bound to alginic acid.

The hydrogel forms by noncovalent crosslinking of the alginic acid with a cation, e.g., $Li^+$, $Mg^{2+}$, $Ca^{2+}$, $Sr^{2+}$, $Ba^{2+}$, $Zn^{2+}$, $Cu^{2+}$, or $Al^{3+}$. A preferred cation is $Ca^{2+}$. Gelation of hydrogels of the invention may be reserved by contact with a chelator for the cation, e.g., EDTA, EGTA, sodium citrate, BAPTA, crown ether, cryptand, phenanthroline sulfonate, dipyridyl sulfonate, dioxane, DME, diglyme, or triglyme. Preferably, the chelator is a bioinert molecule such as EDTA, which is well-known not to interfere with cell growth and proliferation pathways at concentrations relevant for complex dissolution.

Separation Unit

Figure 2:
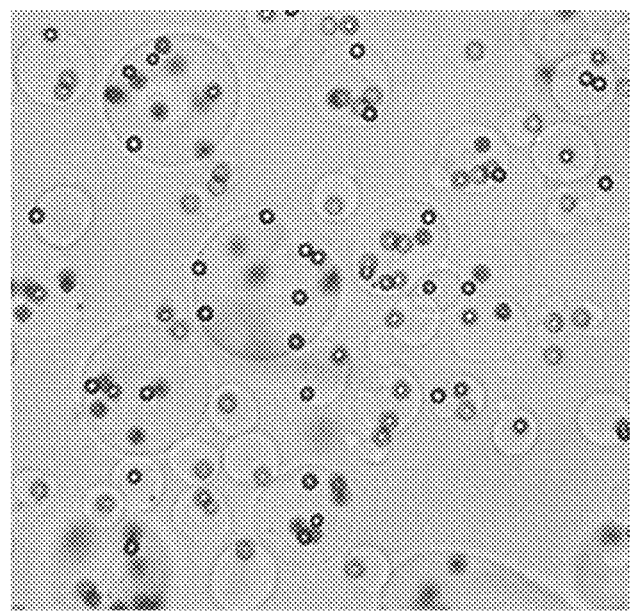
FIG. 2: Light microscope image showing complexes of the present invention, which include a magnetic bead substrate (i.e., one or more magnetic particles) encapsulated within an alginic acid hydrogel.
Figure 3:
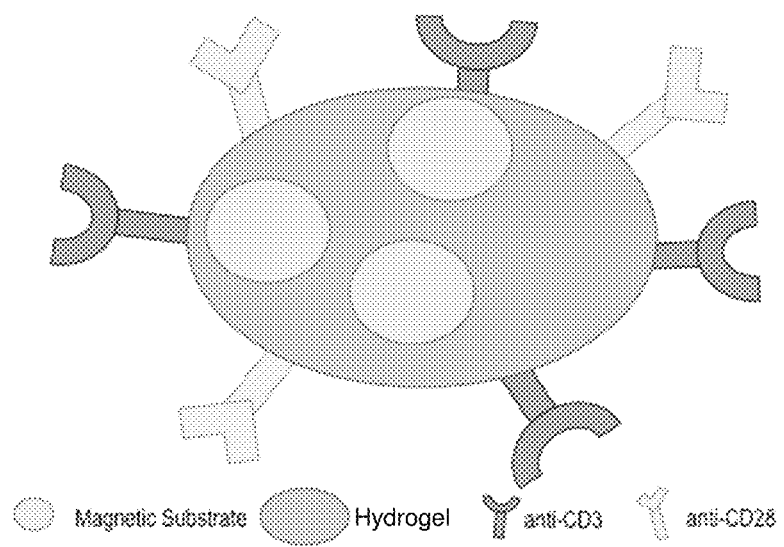
FIG. 3: A schematic showing complexes of the present invention, which includes, in addition to a magnetic bead substrate, anti-CD3 and anti-CD28 surface moieties.

The complex of the present invention can be formulated by gelation of the hydrogel around a separation unit. For example, the hydrogel may be formulated as a coating on the outer surface of the separation unit. Preferably, the separation unit can include multiple smaller structures that are encapsulated within the hydrogel matrix, as shown in FIGS. 2 and 3.

The separation unit can be any structure that enables the user to physically manipulate the position of the target cells, once bound with the complex of the invention. Preferably, the separation unit can include one or more magnetic elements to enable physical manipulation, separation, or purification of target cells. Preferably, the magnetic element is encapsulated within a polymeric or hydrogel structure, such that its movement along a magnetic field functions to pull the complex, along with any attached cell, through the field. The magnetic element can be one or more microparticles or nanoparticles having magnetic properties. Methods for making magnetic microparticles and nanoparticles and integrating them within polymeric complexes are described in the art (WO 2003/071561, WO 2003/086660, WO 2004/060580, U.S. Pat. No. 7,691,285, U.S. P.G. Pub. 2004/0099954, WO 2001/017662, WO 2002/043708). Magnetic particles can be ferrite, oxide, or metallic, and they can be superparamagnetic. Magnetic nanoparticles are often iron oxides, such as magnetite ($Fe_3O_4$) or maghemite ($Fe_2O_3$). Magnetic particles can have a shell, such as a polymer shell. The precipitation of iron oxides can occur under non-aqueous conditions (U.S. Pat. No. 4,677,027) and subsequently be converted to aqueous conditions (U.S. Pat. No. 5,160,725) or can occur exclusively in aqueous solutions (U.S. Pat. No. 4,329,241). Aqueous formulations may preferable in biological applications because of toxicological considerations (U.S. Pat. No. 4,101,435). Wet chemical synthesis of the iron oxide crystallites can precede coating with polymer components (core-shell method) or can occur in the presence of the polymer (one-pot method).

In one aspect of the invention, the separation unit can be removed from the target T cell population. This separation can occur in response to exposure of the complex to a cation chelator as discussed above, which results in release of the separation unit from the binding unit.

Synthesis

The compositions of the present invention can be synthesized by methods currently known in the art. Preferably, complexes can be formulated as microparticles by one of several known methods (e.g. microemulsion). Techniques useful in encapsulating nanoparticles (i.e. magnetic nanoparticles) within polymeric microparticles are disclosed, for example, in U.S. 2011/0229580. Other methods that can be used to entrap a separation unit (i.e. magnetic particles) within a hydrogel include coating by, e.g., dipping, painting, or spraying, with a liquid alginic acid composition and then contacting with cations for crosslinking, e.g., by dipping painting or spraying. Methods for synthesizing alginate beads for various applications are known in the art (see, for example, Hatch, et al., *Langmuir* 27 (2011): 4257-4264 and Sosnik, *ISRN Pharmaceutics* (2014):1-17). Alginate PEG co polymer is synthesized using aminated PEG combined in a batch reaction of Alginic acid, EDC, and sulfo NHS. Antibody conjugation is performed using standard bio conjugation techniques including malidimide/thiol and EDC/NHS linking. Other useful conjugation methods are described in Hermanson et al., (2013) Bioconjugate Techniques: Academic Press.

Methods of Use

The invention features a method of activating a population of T cells using the complex described above. In one aspect of the invention, T cell activation or expansion can be performed by isolation of T cells and subsequent stimulation followed and/or expansion. Prior to expansion, a source of T cells can obtained from a subject. T cells can be obtained from a number of sources, including peripheral blood mononuclear cells, bone marrow, lymph node tissue, spleen tissue, and tumors. In certain embodiments of the present invention, a T cell line available in the art may be used. T cells can also be obtained from a unit of blood collected from a subject using any number of techniques known to the skilled artisan, such as Ficoll separation or through a PERCOLL® gradient. Cells from the circulating blood of an individual can be obtained by apheresis or leukapheresis. The apheresis product typically contains lymphocytes including T cells, monocytes, granulocytes, B cells, other nucleated white blood cells, red blood cells, and platelets. The cells collected by apheresis may be washed to remove the plasma fraction and to place the cells in an appropriate buffer or media for subsequent processing steps. T cells can be enriched prior to treatment with the complex of the present invention through conventional techniques such as magnetic bead negative selection or fluorescence activated cell sorting (FACS). T cells can be antigen-specific, antigen-nonspecific, or tumor specific. They can include populations of CD4 cells, CD8 cells, NK T cells, or, for autoimmune or transplant rejection therapies, regulatory T cells.

In addition to purification steps, T cells that have been obtained from a subject may be further processed prior to or after incubation with the complex of the present invention. For example, cells can undergo genetic engineering to equip them with certain functional characteristics, such as in the process of chimeric antigen receptor (CAR) engineering, which equips a patient's cells to recognize cancer antigens. In this case, the CAR engineering procedure may be performed prior to treatment with the present complexes in order to expand the initially small number of CAR T cells into a substantial activated population. Other genetic procedures used for adoptive therapy are discussed in Rosenburg et al. (*Nat Rev Cancer* 8 (2008): 299-308). In other cases, such as those not involving genetic modification, such as bispecific T cell engager (BITE) technology (see WO2011/057124), such procedures may be performed after the cells have been expanded using the present invention. Other non-genetic processing procedures include but are not limited to treatment with IL-2, IL-4, IL-7, IL-10, IL-12, IL-15, IL-21, or TGF-β.

Sample Treatment

In one aspect of the invention, the starting T cell population is incubated with the complexes. The ratio of complexes to starting cell number will depend on the size and shape of the complex. For this purpose, it will be understood by a person of skill in the art that the ratio of surface area between target T cells and complexes is a significant factor governing the degree of resulting T cell activation. Preferably, the surface area ratio between target cells and complexes is between about 1:100 and about 100:1 (e.g., about 1:100, about 1:80, about 1:50, about 1:25, about 1:10, about 1:5, about 1:4, about 1:3, about 1:2, about 1:1, about 2:1, about 3:1, about 4:1, about 5:1, about 10:1, about 25:1, about 50:1, about 80:1, or about 100:1). Other factors which should be considered when incubating starting T cells with complexes are the density of binding moieties on the complex surfaces, the specific binding moieties chosen (i.e., their binding affinity, EC50, receptor concentration on T cells, etc.). Additionally, it will be appreciated that as T cells proliferate over the course of multiple days, their volumetric requirements will increase, which may limit the total volume that can be allocated to complexes.

Incubation Procedures

Methods of the present invention include incubating T cells with complexes in a suitable vessel. Such cell-culture vessels are known in the art and can include cell culture plates, flasks, or bioreactors of any suitable size. Cell culture vessels are preferably sterile, and may be configured for optimal gas exchange or media exchange, such as perfusion capable systems, which are known in the art. T cells can be seeded at a concentration of between about $0.2 \times 10^6$ and $10 \times 10^6$ cells/ml. Complexes may require special ionic conditions, e.g., to maintain a solid structure in solution. For example, cell culture media can be supplemented with ions, such as $Ca^{2+}$, through addition of salts, e.g., $CaCl_2$. Ions can be present at any physiologically suitable concentration (e.g., 1.0 nM-100 mM, e.g., 1.0 μM to 10 mM, e.g., 0.1 mM, 0.2 mM, 0.5 mM, 1.0 mM, 2 mM, 3 mM, 4 mM, 5 mM, 6 mM, 7 mM, 8 mM, 9 mM, or 10 mM).

Kinetics

Ex vivo T cell expansion protocols are well-developed, especially for human samples, and can often yield cell number increases in the hundred-fold range, over the course of multiple weeks of culture. Thus, multiple rounds of expansion may be required to overcome constraints on physical space and media nutrient depletion. To accommodate these constraints, the complexes of the present invention can be dissolved (i.e., the separation unit removed) multiple times (e.g., once, twice, or 3-12 times) over the course of a T cell expansion protocol. Such dissolution/re-administration cycles can be achieved by washing out cation chelators from the media by centrifugation or other known methods after each dissolution. Alternatively, additional complexes can be introduced into the cultures without removing separation units of the existing complexes, thus bypassing the need for media changes. If necessary, beads encapsulating magnetic particles, or excess magnetic particles alone, can be removed from cultures using well-established magnetic separation procedures.

In one aspect of the present invention, the T cell expansion protocol proceeds for a predetermined length of time that is suitable to generate a desired number of T cells, a representative phenotype, or both. Alternatively, the phenotypic properties of T-cell populations of the present invention can be monitored by a variety of methods, and the isolation can be performed after the desired phenotype is acquire. Relevant phenotypes are metabolic changes such as biochemical or morphological changes (e.g., change in frequency of cell division, change in cytokine expression profile, change in median cell diameter, change in surface molecule expression, or change in cellular motility). Assays for monitoring such changes include standard flow cytometry methods, ELISA, microscopy, migration assays, metabolic assays, and other techniques known by those skilled in the art.

In some cases, the methods of the present invention allow for expansion of a population of cells containing naïve T cells, central memory T cells, and/or effector memory cells. As discussed above, the composition of the polymeric moiety can influence the percentage and/or total number of naïve T cells, central memory T cells, and/or effector memory cells present in a population (e.g., an expanded population). For example, by culturing a starting population of T cells with a complex having a low-elastic modulus polymeric moiety (e.g., an alginic acid-based polymeric moiety having an elastic modulus less than 100,000 Pa, less than 50,000 Pa, less than 10,000 Pa, less than 5,000 Pa, or less than 1,000 Pa, at one or more points in time over the course of incubation with the cells) a resulting population of T cells may include a high percentage of naïve T cells (e.g., naïve CD4$^+$ T cells or naïve CD8$^+$ T cells). In some instances, naïve T cells are characterized as having one or more properties (surface markers or secreted cytokines) of Table I (see Examples).

Purification

Alginic acid provides a physical anchor to entrap the separation unit. In the presence of a cation, e.g., calcium, alginic acid is crosslinked and solid. Upon completion of T cell processing, the hydrogel can be dissolved using a chelator to release the separation unit from the T cell. In some aspects, the separation unit includes magnetic particles that are not permissible as part of clinical samples (e.g. the resulting activated T cell suspension). By releasing the separation unit (e.g. magnetic particles) by cation chelation, the resulting T cells are efficiently cleaned of potentially harmful impurities and ready for infusion into a patient in need thereof.

EDTA is a well-characterized calcium chelator of use in the present invention. EDTA can be used at 2 mM in the form of a physiologically insert buffer that preferably also contains 137 mM NaCl, 2.7 mM KCl, 25 mM Hepes and 0.75 mM $Na_2H_2PO_4 \cdot 2H_2O$.

Cell culture media can be exchanged for the ion chelator solution, e.g., EDTA buffer, potentially by centrifugation and subsequent resuspension of cell pellet, e.g., in EDTA buffer. Other methods may also be used. The cell/ion chelator suspension may also be agitated, e.g., by pipetting or vortexing for about 5 seconds. Cell suspension can be placed on a magnetic stand for long enough to allow separation of all magnetic particles from cells (5 minutes is typical). During this step, the hydrogel dissolves, cells are released, and the magnetic particles are attracted to the side of the vessel being used (e.g. tube). With the cell suspension still on the magnetic stand, the supernatant can be changed to a clean tube, while magnetic particles can be left behind. This step can be repeated again in the initial tube in order to recover any cells that remain attached to magnetic particles. The isolated cells can then be returned to cell culture media or isotonic solution (e.g., for administration into a patient).

EXAMPLES

FIG. 1 shows a workflow for the manufacture of chimeric antigen receptor (CAR) T cells using CD3/CD28 complexes for T cell activation and expansion. First, T cells can be isolated from the patient and engineered to express CARs that recognize cancer cells. At this point, anti-CD3/anti-CD28 complexes can be added to CAR T cells, which will facilitate activation and expansion. Post expansion, the complex can be dissolved away leaving T cells magnetic-label free, increasing viability and reducing the potential for a negative host response.

FIG. 2 is a light microscope image showing complexes of the present invention, which include a magnetic bead substrate coated with an alginic acid hydrogel. The hydrogel is a novel dissolvable polymer, which has the ability to be conjugated with ligands to facilitate the attachment and subsequent release of targeted cell types.

FIG. 3 is a schematic of a complex of the present invention, which includes a magnetic bead substrate coated with an alginic acid hydrogel, which has been conjugated with anti-CD3 and anti-CD28 ligands.

Figure 4:
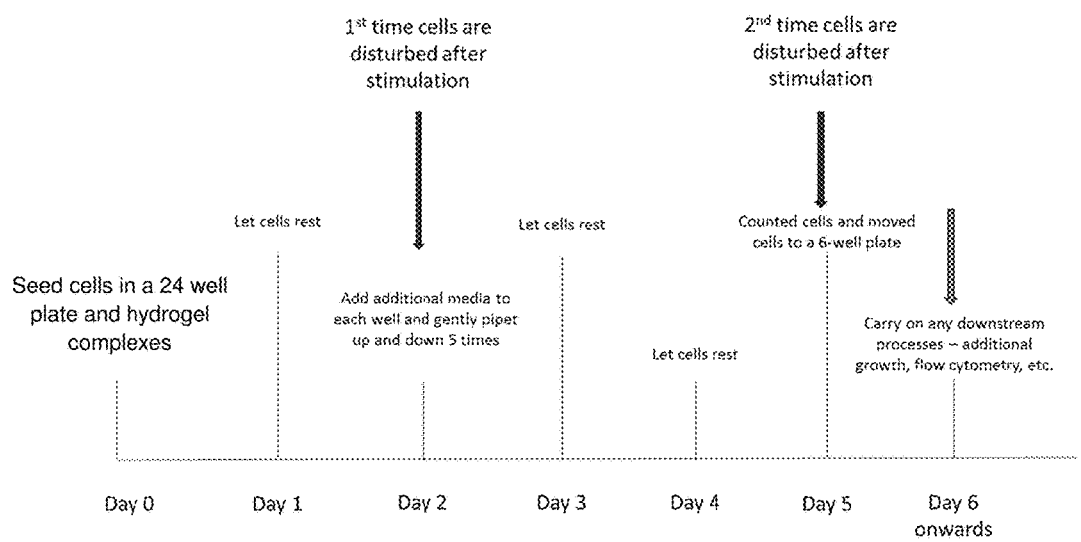
FIG. 4: A timeline showing a sequence of procedures involved in an exemplary protocol for setting up an experiment using the complexes of the invention.

FIG. 4 shows an exemplary timeline of procedures carried out to prepare a T cell population with hydrogel complexes of the present invention. At day 0, cells are seeded in a 24 well plate with hydrogel complexes. At day 2, additional media is added to the cells and the culture is mixed by gently pipetting up and down five times. At day 5, cells are counted and transferred to a six-well plate, where they are cultured in experiment-specific conditions or allowed to continue growth.

Figure 5:
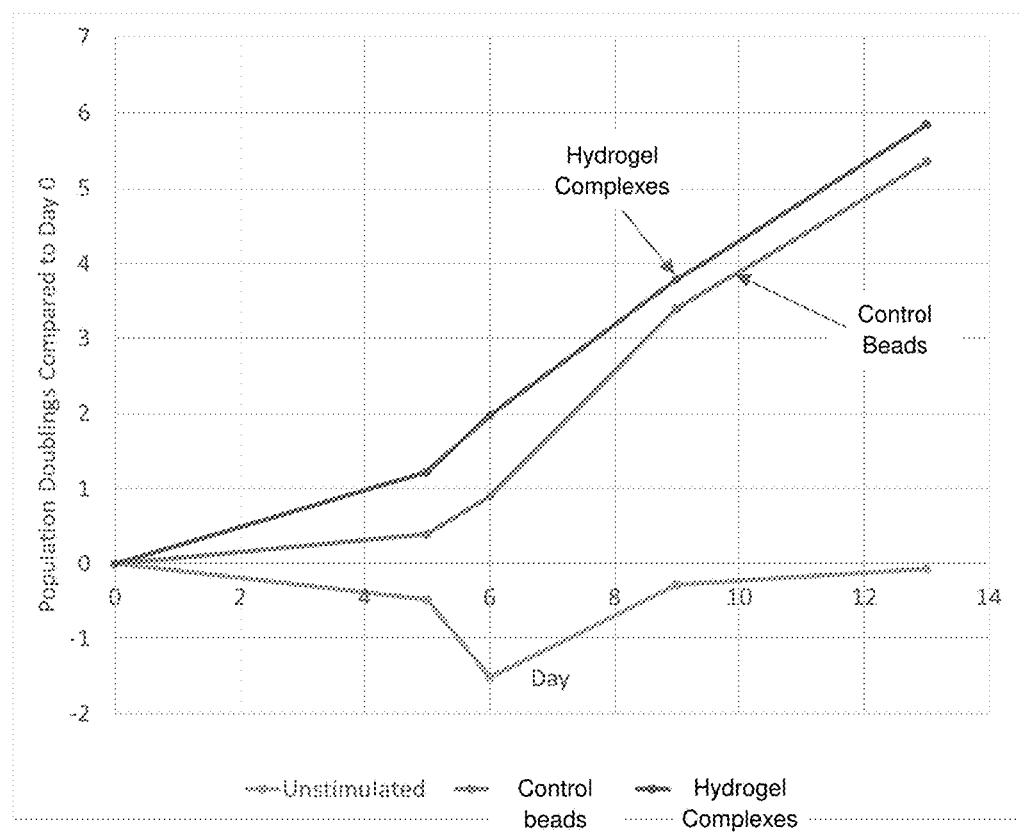
FIG. 5: A graph showing the induction of human T cell expansion by complexes of the invention in comparison with control beads (anti-CD3/CD28-coated beads) and untreated controls.

FIGS. 5-17 show characteristics of T cell populations treated using methods of the invention, in comparison to conventional methods involving commercially available anti-CD3/CD28 magnetic beads (control). Primary human T lymphocytes were seeded at a density of $1 \times 10^6$ cells/mL and cultured in advanced RPMI medium supplemented with fetal bovine serum, glutamate, HEPES, and recombinant human IL-2. For the hydrogel complex-treated cells, the media was further supplemented with 2 mM $CaCl_2$. On day one of culture, cells were stimulated with either control beads at a concentration of one bead per cell or with two different formulations of hydrogel complexes coated with anti-CD3 and anti-CD28 antibodies (Affymetrix/ebioscience). Subsequently, media was replenished every 2-3 days without further addition of control beads or hydrogel complexes. In response to stimulation, T cells expanded potently and in a sustained manner (FIG. 5). Cells proliferated to a similar degree whether they were treated with control beads or hydrogel complexes. In unstimulated cells, no cell expansion occurred.

Figure 6A:
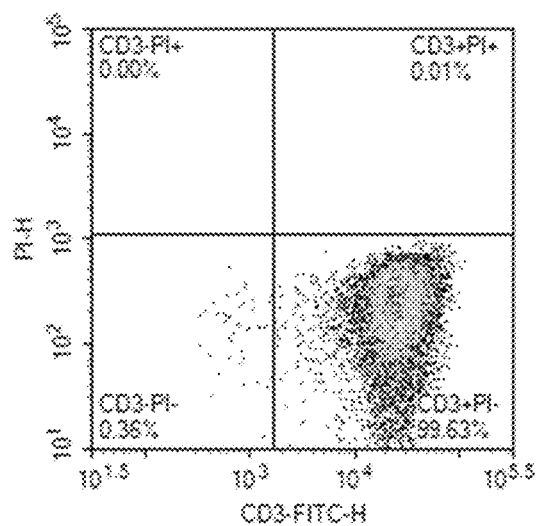
FIGS. 6A and 6B: Flow cytometry plots showing the phenotype of T cells expanded by complexes of the invention.
Figure 6B:
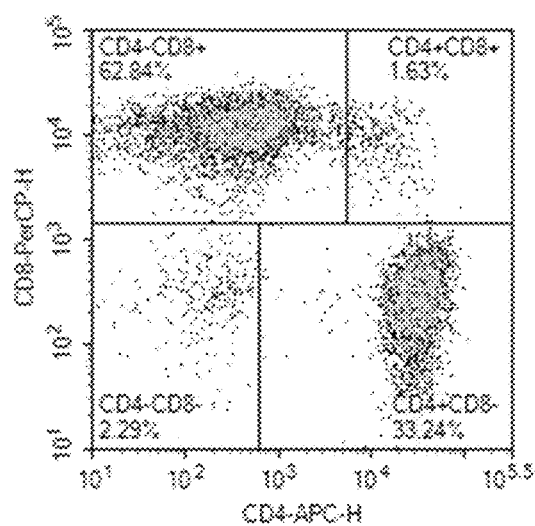
Figure 7A:
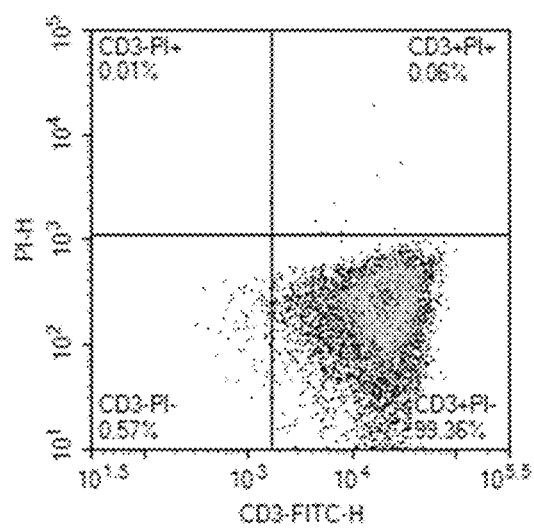
FIGS. 7A and 7B: Flow cytometry plots showing the phenotype of T cells expanded by control beads (anti-CD3/CD28-coated beads).
Figure 7B:
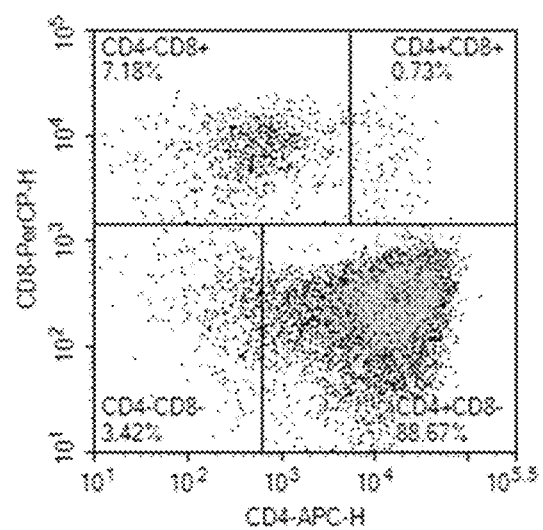
Figures 8A, 8B:
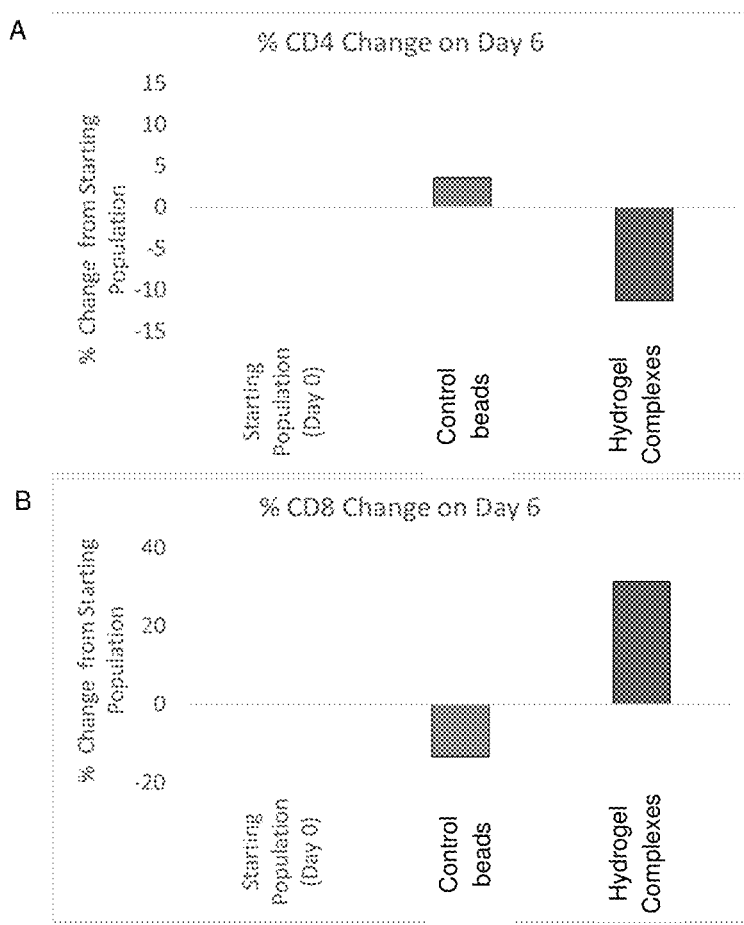
FIGS. 8A and 8B: Bar graphs showing the percent (%) change in populations of CD4 cells (FIG. 8A) and CD8 cells (FIG. 8B) over the course of expansion with control beads versus complexes of the invention. The data were derived from flow cytometry data analyzed as shown in FIGS. 6 and 7.
Figure 9A:
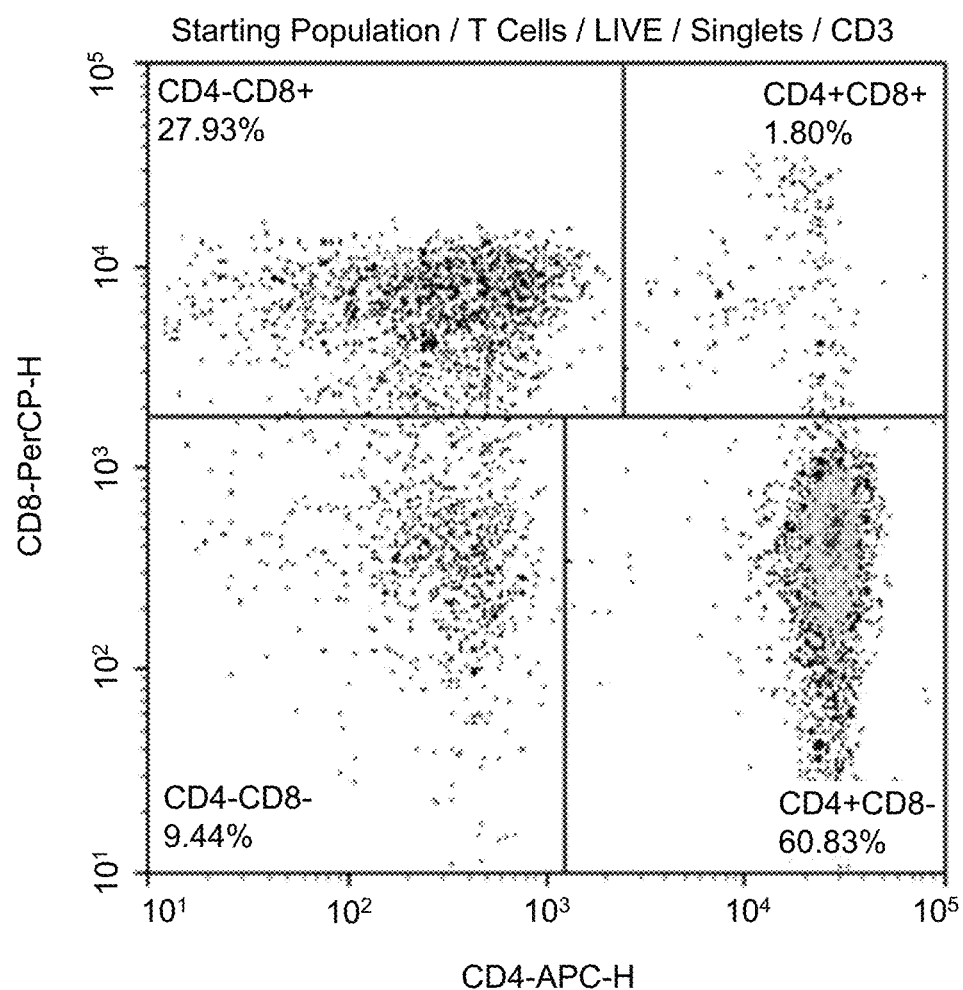
FIGS. 9A-9E: Flow cytometry plots showing the phenotype of T cells at day 0 (a starting population).
Figure 9B:
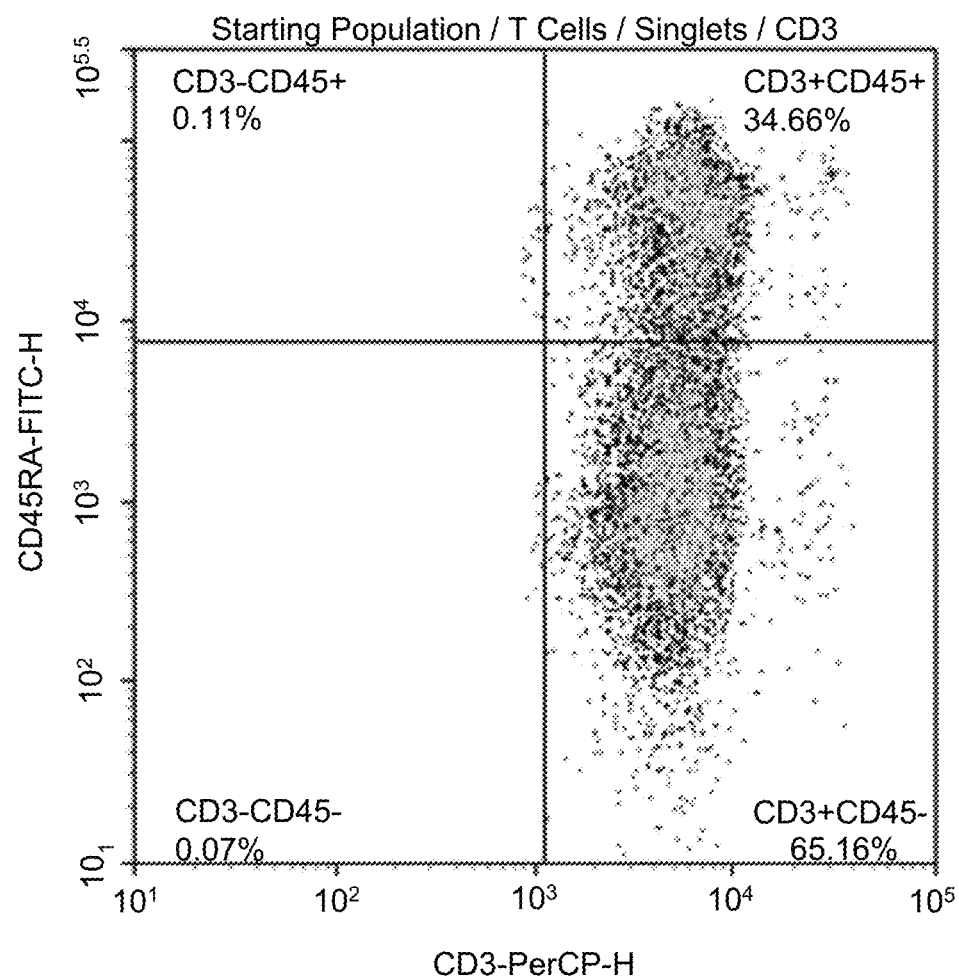
Figure 9C:
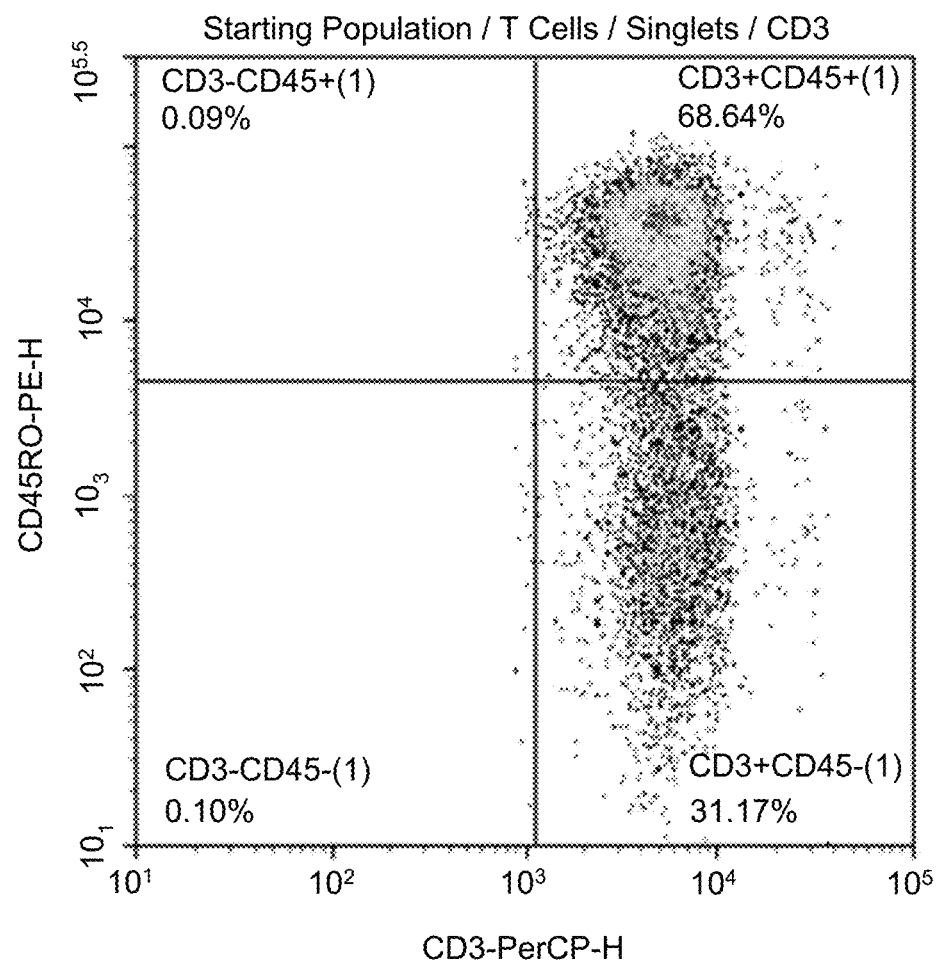
Figure 9D:
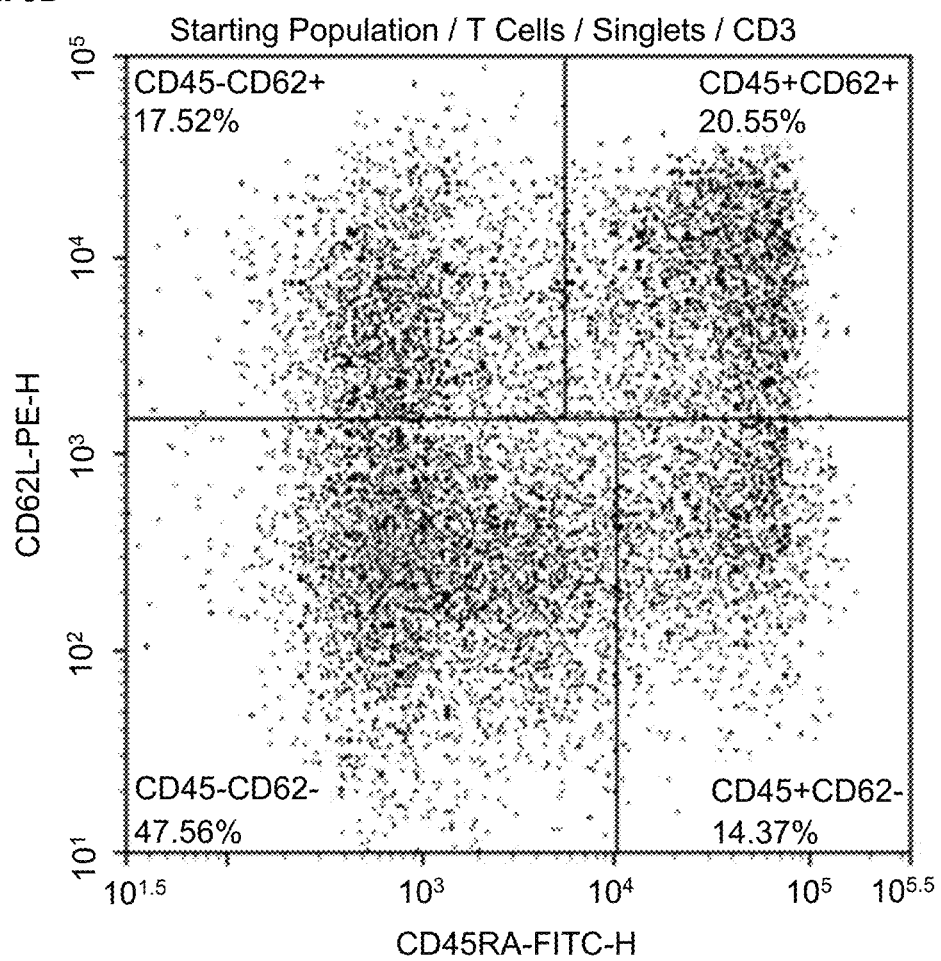
Figure 9E:
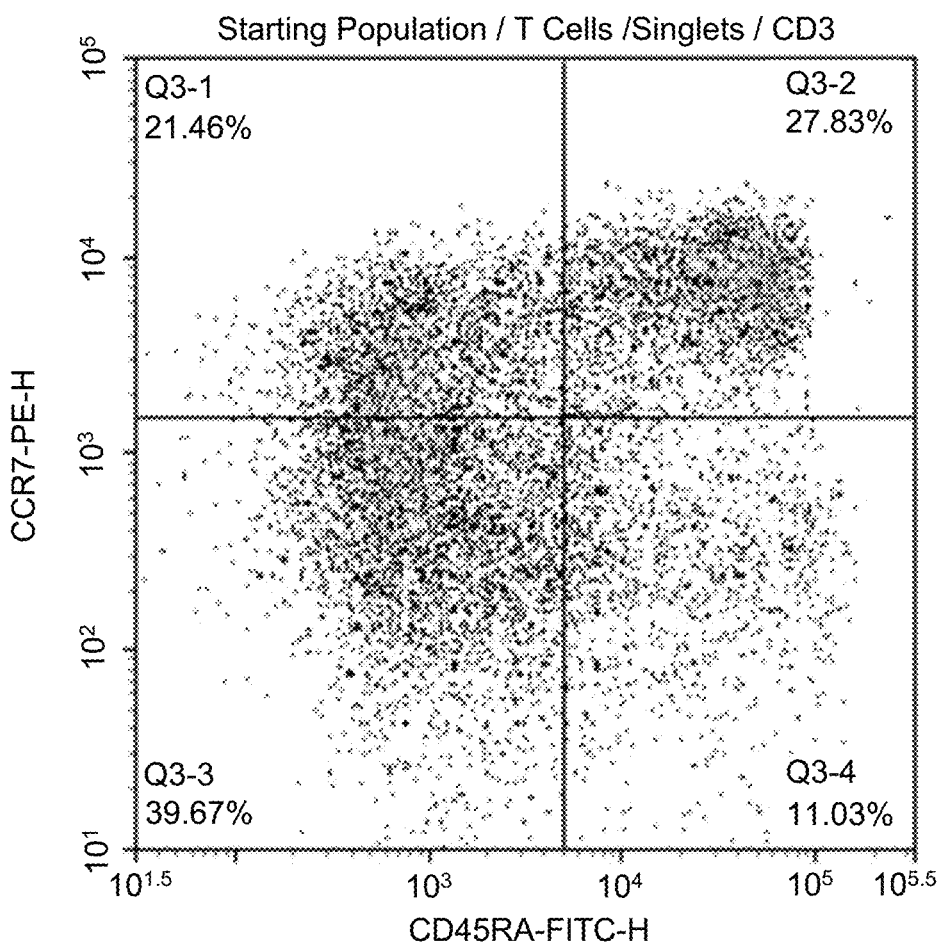
Figure 10A:
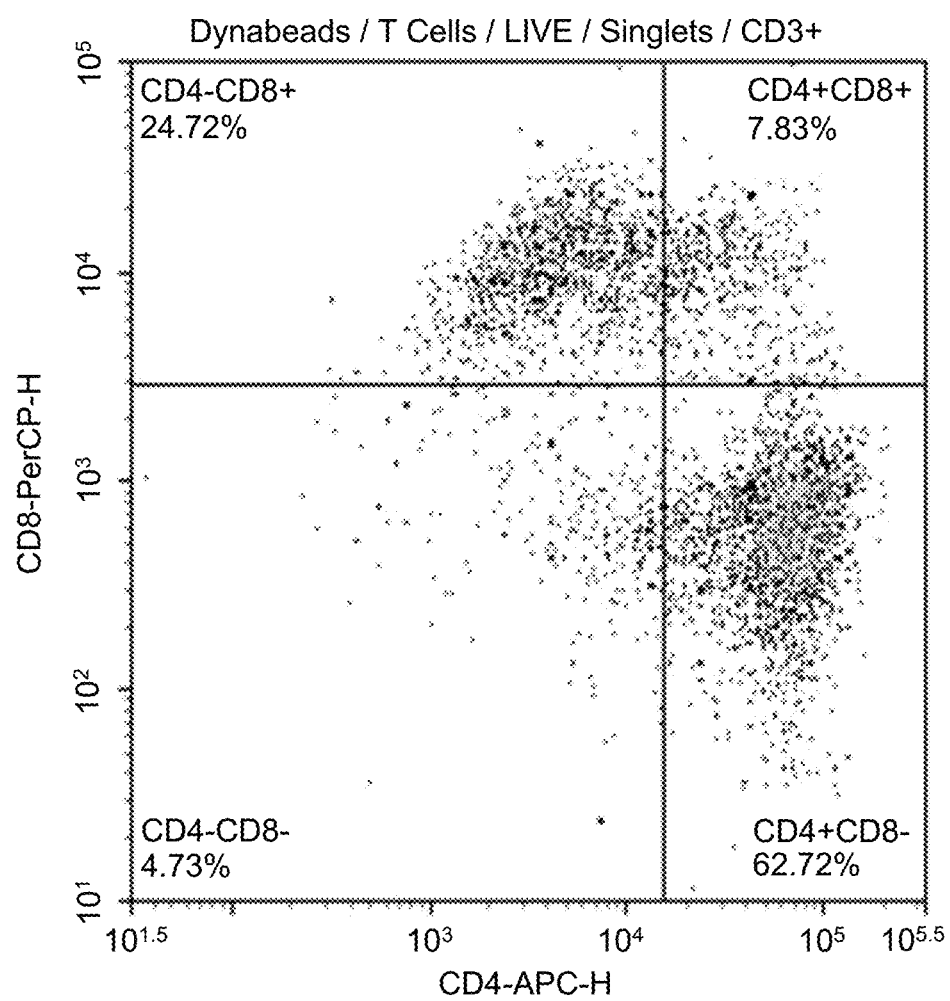
FIGS. 10A-10E: Flow cytometry plots showing the phenotype of control bead-expanded T cells at day 12 of culture.
Figure 10B:
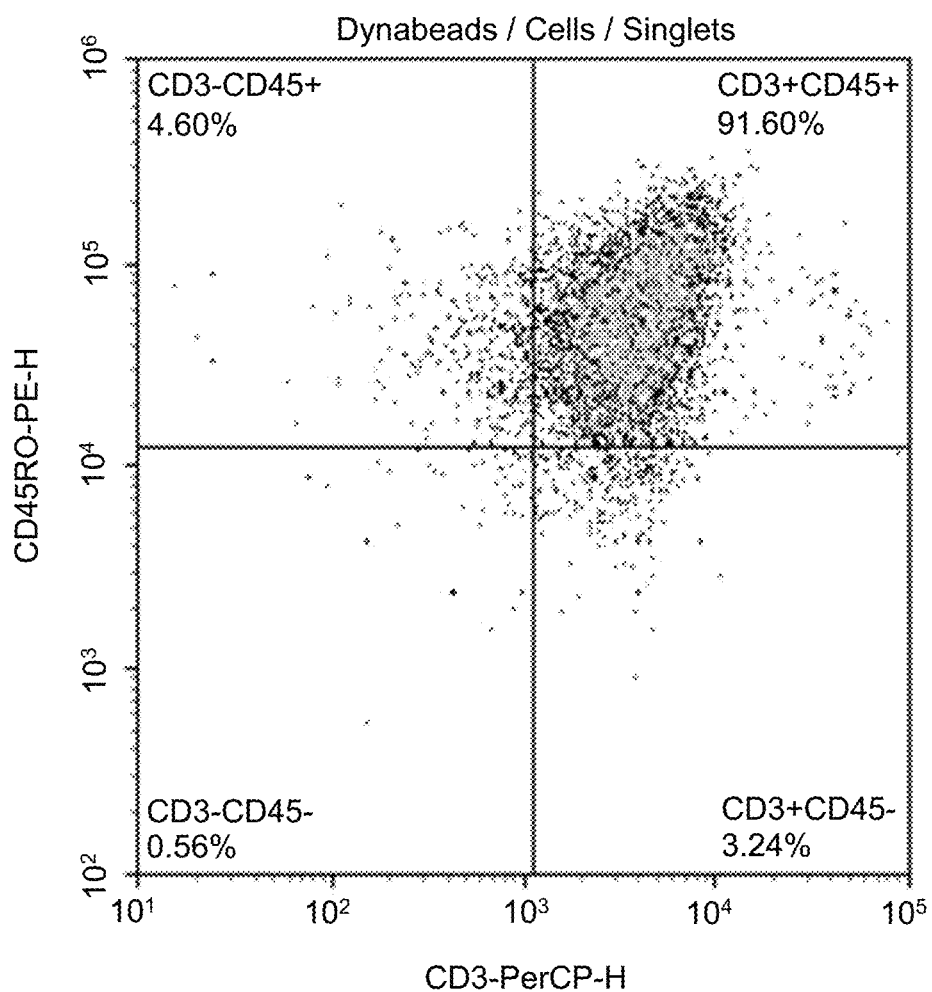
Figure 10C:
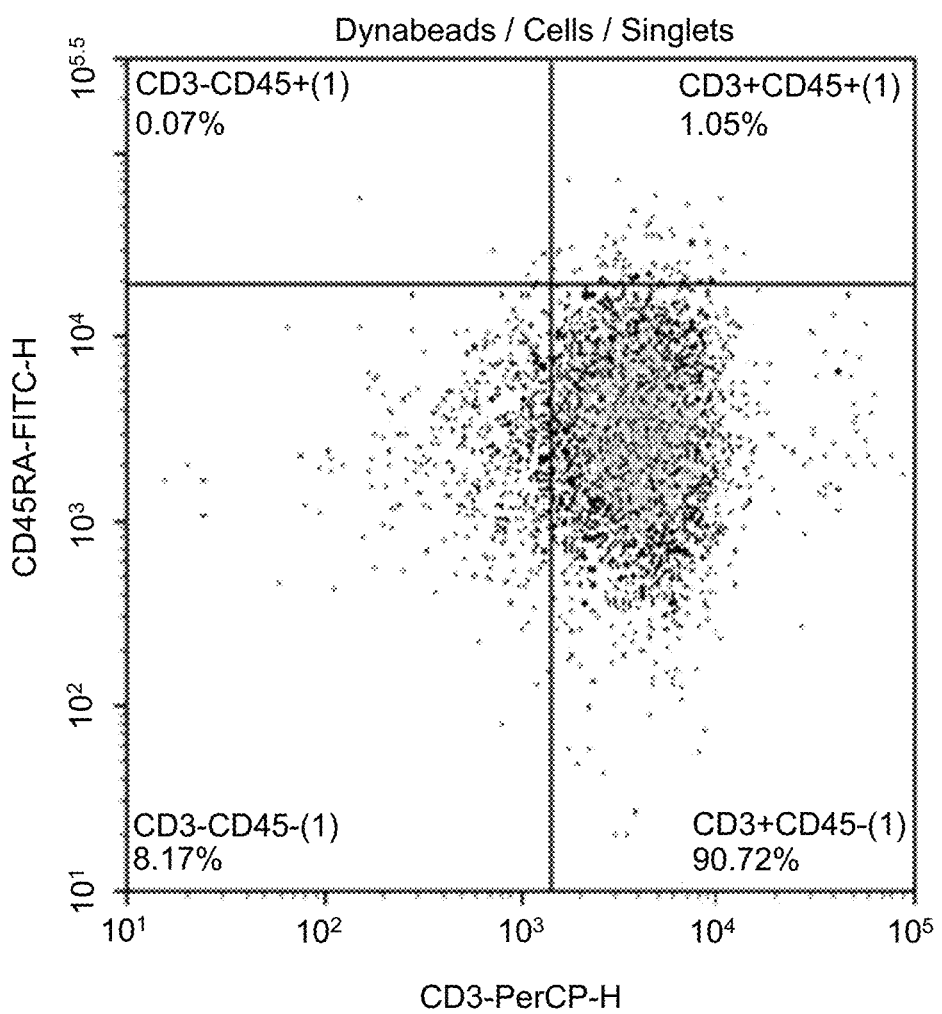
Figure 10D:
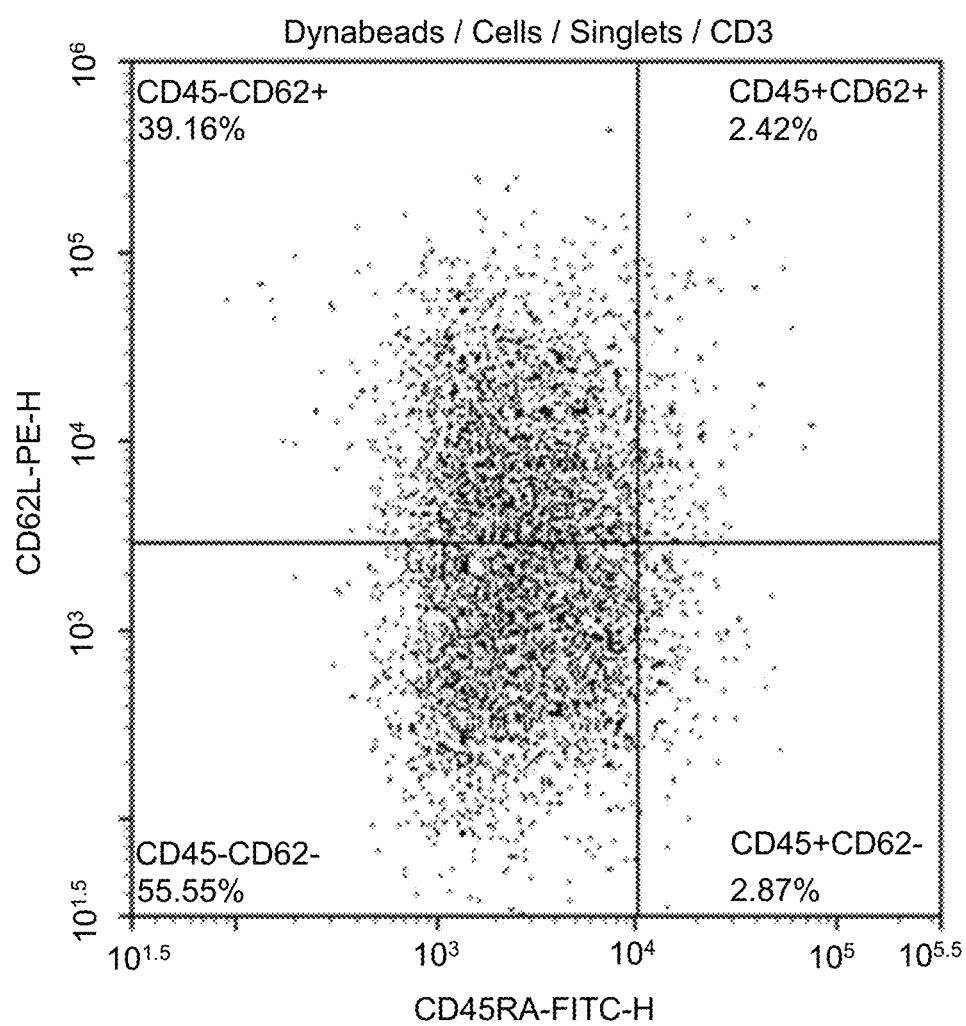
Figure 10E:
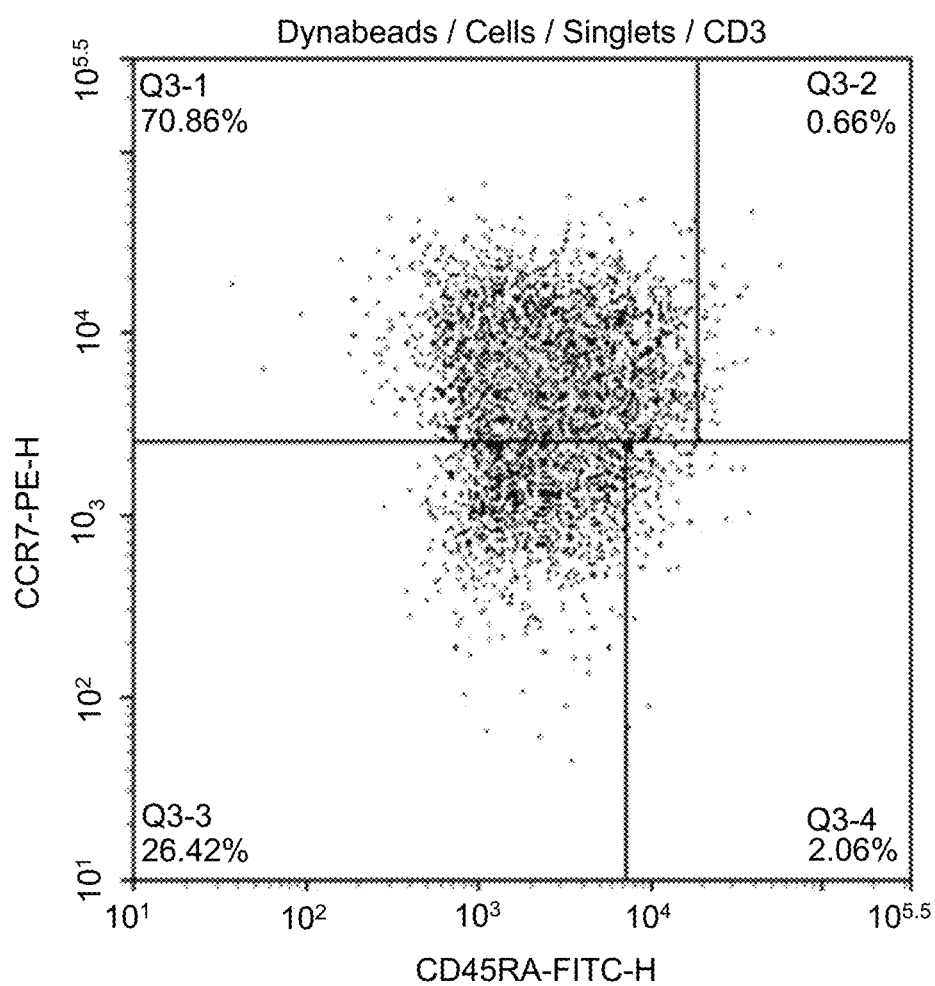
Figure 11A:
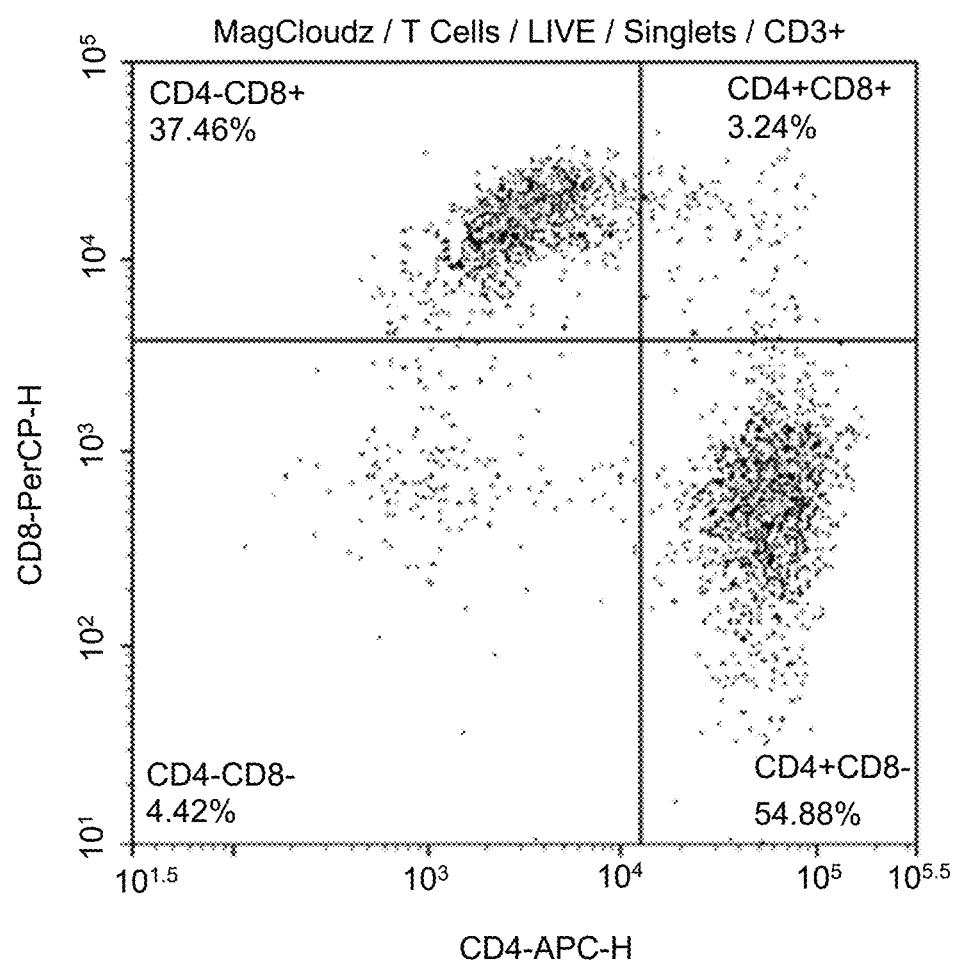
FIGS. 11A-11E: Flow cytometry plots showing the phenotype of T cells expanded by the complexes of the invention at day 12 of culture.
Figure 11B:
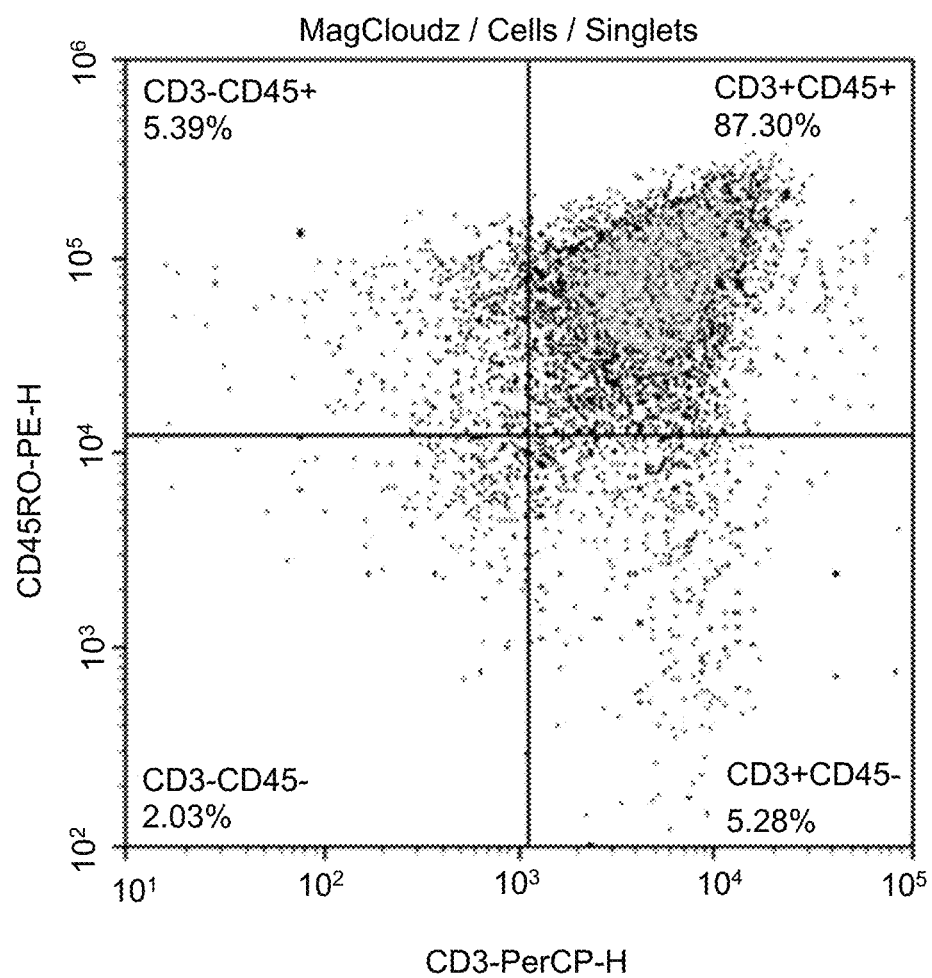
Figure 11C:
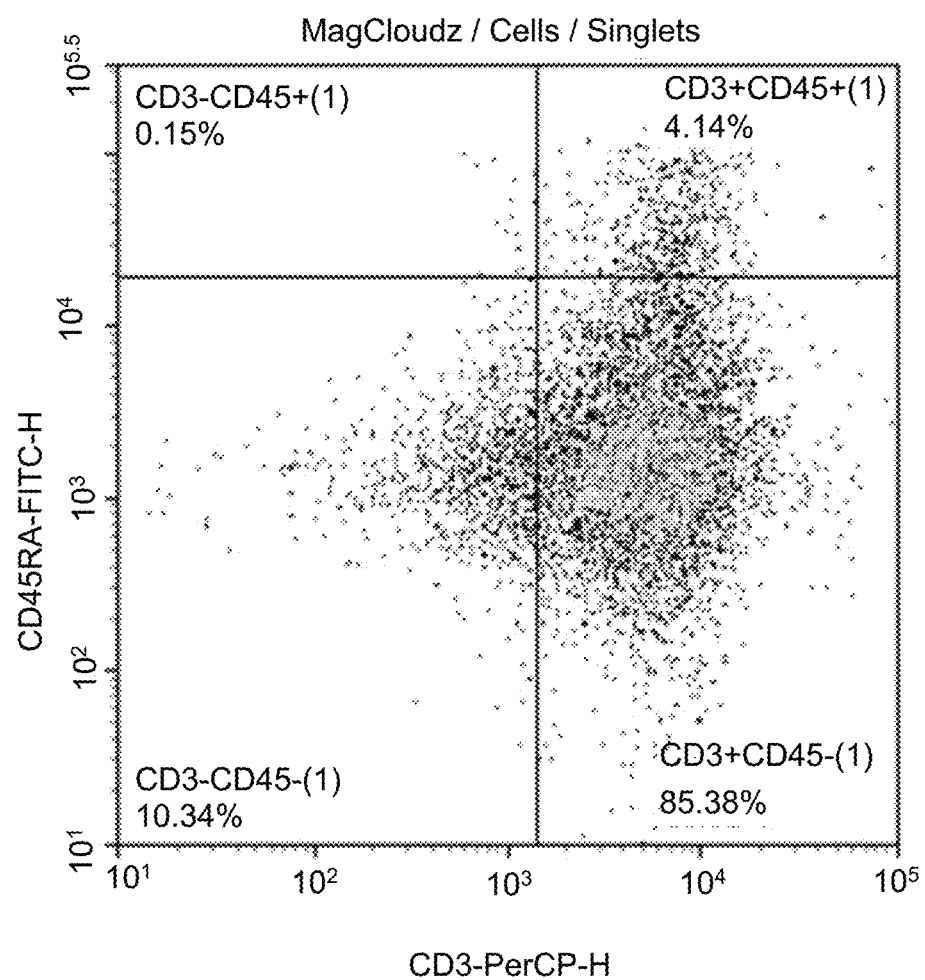
Figure 11D:
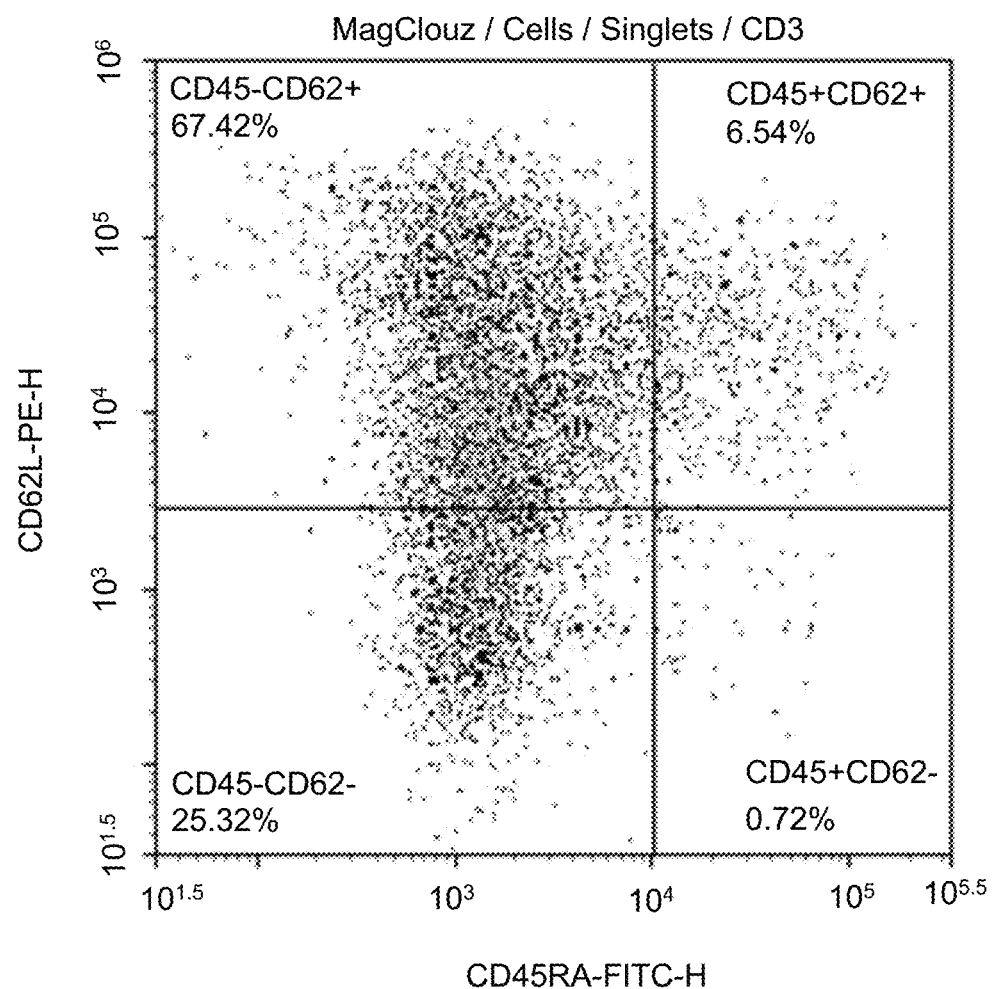
Figure 11E:
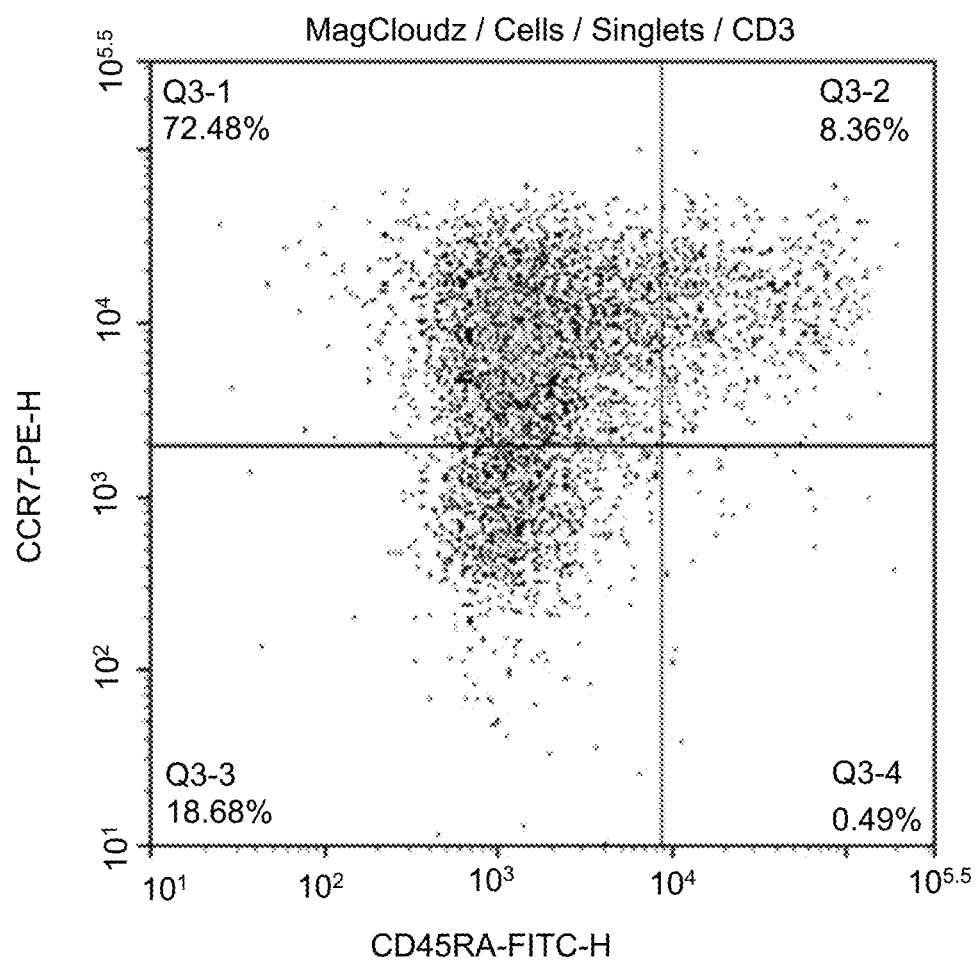
Figure 12A:
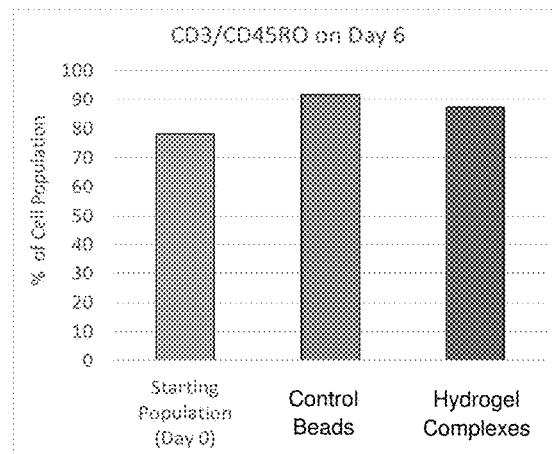
FIGS. 12A and 12B: Bar graphs showing the percent of $CD3^+CD45RO^+$ cells at day 0 versus day 6 of expansion with control beads versus complexes of the invention. The data were derived from flow cytometry data analyzed as shown in FIGS. 10 and 11.
Figure 12B:
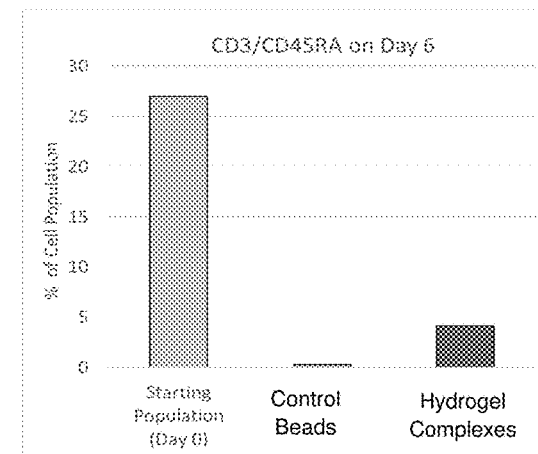

After a twelve-day T cell expansion, cells were stained for viability using propidium iodide. Cell viability was high (greater than 99%) in both hydrogel complex-expanded T cells (FIG. 6A) and control bead-expanded T cells (FIG. 7A). Live samples of each expanded population were then analyzed for surface expression of T cell markers CD3, CD4, and CD8 (FIGS. 6-8). Under each expansion condition, greater than 97% of cells expressed CD3 (FIGS. 6A and 7A). Cells expanded using hydrogel complex formulation #1 were 33.24% CD4-positive and 62.84% CD8-positive (FIG. 6B). T cells expanded by control beads preferentially expressed CD4, relative to T cells expanded by hydrogel beads (FIG. 7B). Control bead-expanded T cells were 88.67% CD4-positive and 7.18% CD8-positive (FIG. 7B). The percentage of cells expressing neither CD4 nor CD8 was less than 5% in all conditions tested. The effect of treatment on CD8 and CD4 expression by T cells is further exemplified by FIGS. 8A and 8B, which show the percent change in CD4 and CD8 expression, respectively, at day 6 of expansion relative to the initial expression levels (e.g., of the starting population at day 0). In hydrogel complex-expanded groups, the percentage of CD4+ T cells decreased by more than 10% from day 0 to day 6, whereas the percentage of CD4+ T cells in the control bead-treated groups increased by about 4% (FIG. 8A). Furthermore, the percentage of CD8+ T cells in the hydrogel complex-expanded groups increased by more than 30%, whereas the CD8+ population of control-treated cells diminished by more than 10% (FIG. 8B).

As summarized in Table 1, below, one current model of T cell development suggest that CD45RA is expressed on naïve T cells and that after antigen experience, central memory T cells and effector memory T cells gain expression of CD45RO and lose expression of CD45RA. According to this model, CD45RA+ cells that simultaneously express CD62L or CCR7 are characterized as naïve T cells.

TABLE 1

Current model of memory T cell subtype marker expression

| T cell subtype | Surface marker expression profile | Secretion profile |
| --- | --- | --- |
| Naïve T cells | CD45RA+ CD45RO− CCR7+ CD62L+ | IL-4− IFN-γ− |
| Central memory T cells | CD45RA− CD45RO+ CCR7+ CD62L+ | IL-4− IFN-γ− |
| Effector memory T cells | CD45RA− CD45RO+ CCR7− CD62L− | IL-4+ IFN-γ+ |

Figure 13:
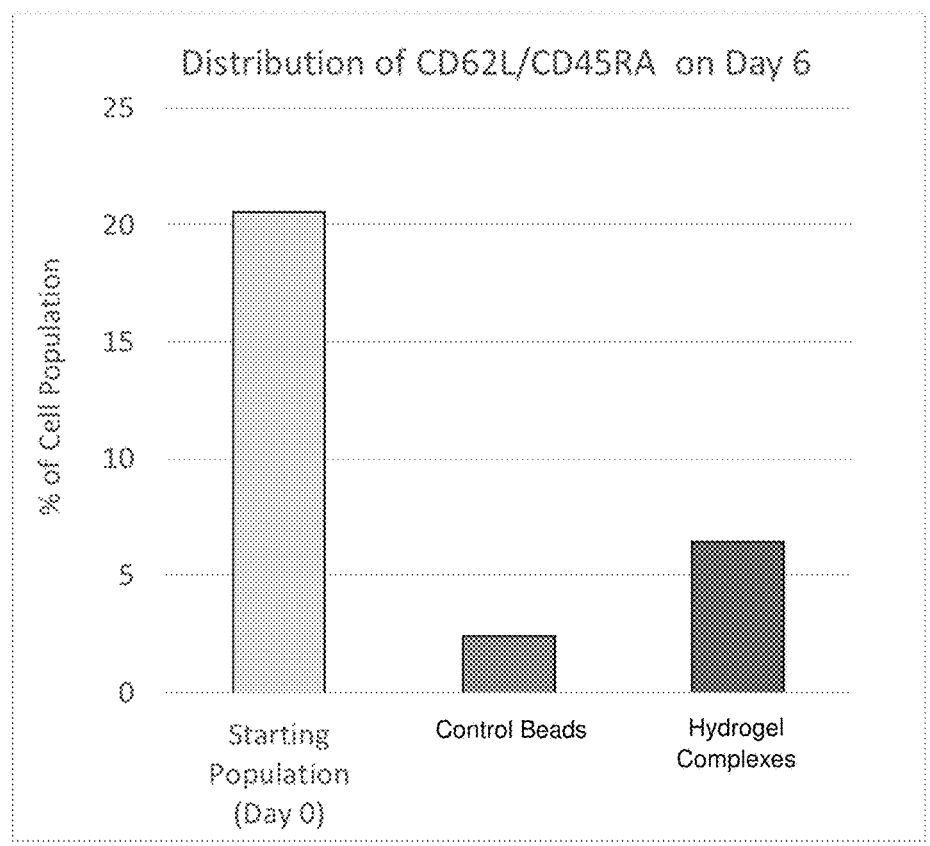
FIG. 13: Bar graph showing the percent of $CD62L^+$ $CD45RA^+$ (naïve) T cells at day 0 versus day 6 of expansion with control beads versus complexes of the invention. The data were derived from flow cytometry data analyzed as shown in FIGS. 10 and 11.
Figure 14:
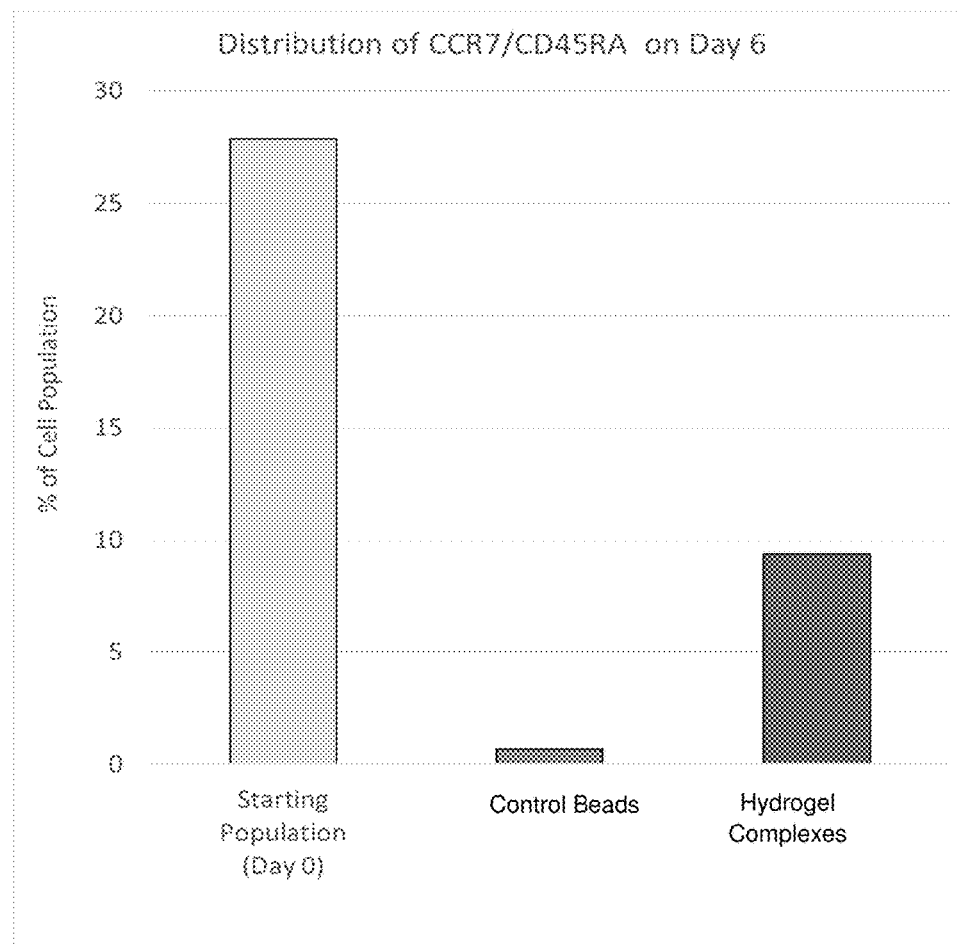
FIG. 14: Bar graph showing the percent of $CCR7^+$ $CD45RA^+$ (naïve) T cells at day 0 versus day 6 of expansion with control beads versus complexes of the invention. The data were derived from flow cytometry data analyzed as shown in FIGS. 10 and 11.
Figure 15:
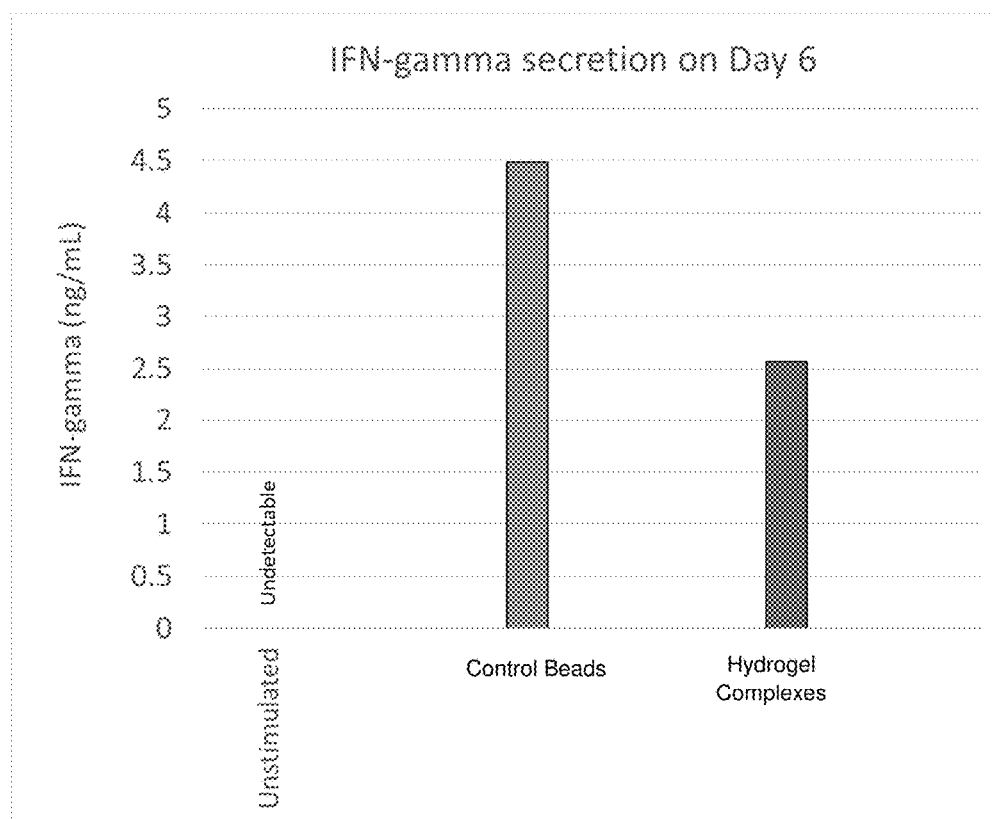
FIG. 15: Bar graph showing the concentration of interferon-gamma (IFN-γ) secreted at day 6 of expansion with control beads versus complexes of the invention, as measured by enzyme-linked immunosorbant assay (ELISA).
Figure 16:
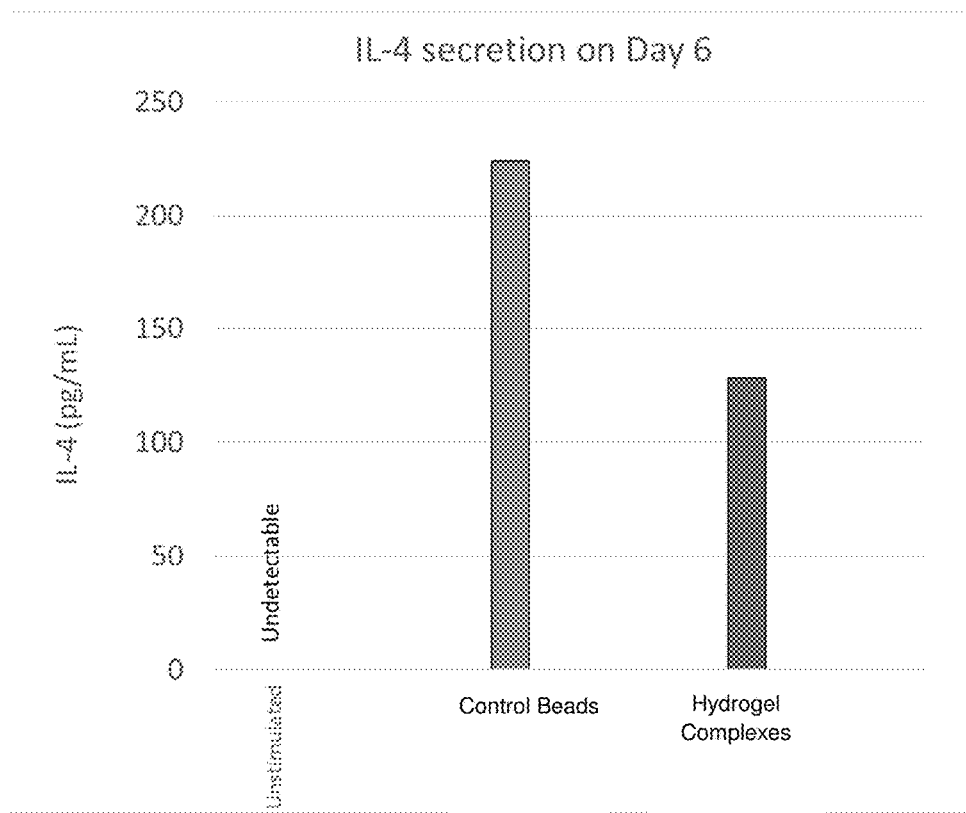
FIG. 16: Bar graph showing the concentration of interleukin-4 (IL-4) secreted at day 6 of expansion with control beads versus complexes of the invention, as measured by enzyme-linked ELISA.

Six days after induction of T cell expansion with control beads (FIGS. 10A-10E) or hydrogel complexes (FIGS. 11A-11E), each expanded population was analyzed via flow cytometry for surface expression of CD3, CD4, CD8, CD45RO, CD45RA, CD62L, and CCR7 and compared with the expression profiles of cells at day 0 (FIGS. 9A-9E). In the CD3+ expanded population, a greater percentage of cells treated with hydrogel complexes were CD45RA+, relative to cells treated with control beads (FIG. 12B), suggesting that treatment with hydrogel complexes preferentially yields naïve T cells. To confirm this observation, dual expression of CD62L and CD45RA was assessed. In the CD3+ expanded population, a greater percentage of cells treated with hydrogel complexes were CD62L+CD45RA+, relative to cells treated with control beads (FIG. 13). Dual expression of CCR7 and CD45RA was also measured in the CD3+ expanded population, and a greater percentage of cells treated with hydrogel complexes were CCR7+CD45RA+, relative to cells treated with control beads (FIG. 14). Thus, hydrogel complexes induced a higher percentage of T cells having a naïve phenotype than control beads, as determined by surface marker expression profile.

As noted in Table 1, the secretion of certain effector cytokines, such as IL-4 and IFN-γ, can be indicative of a T cell's effector memory phenotype. Six days after induction of T cell expansion with control beads or hydrogel complexes, samples of cell culture medium were harvested and analyzed for the presence of IL-4 and IFN-γ by ELISA. Medium from hydrogel complex-treated cultures contained lower quantities of IFN-γ (FIG. 15) and IL-4 (FIG. 16), relative to control bead-treated cultures, reflecting a smaller population of effector memory T cells within the hydrogel complex expanded population.

Figure 17:
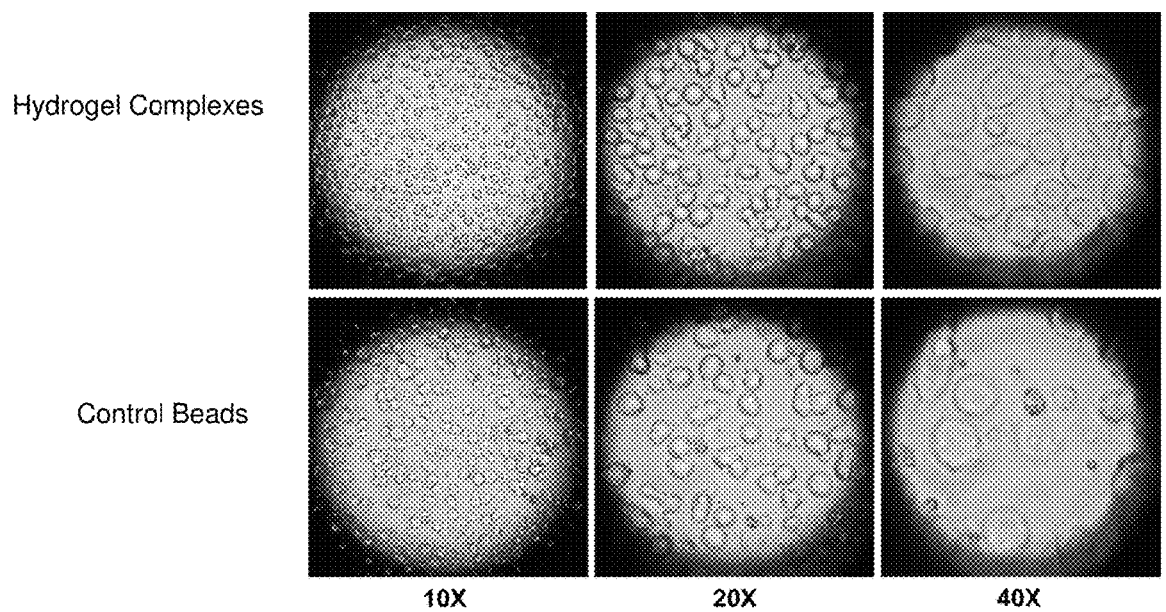
FIG. 17: A series of light microscope images showing T cells expanded by complexes of the invention in comparison with control beads.

Lastly, it was demonstrated that separation of expanded T cells from hydrogel complexes can be performed simply and efficiently. The top panels of FIG. 17 show hydrogel complex-expanded T cell cultures following hydrogel dissolution and removal. After 7 days of culture in the presence of hydrogel complexes, 5 mM EDTA was added to the culture medium, and cells were briefly agitated. Following agitation, cultures were placed on a cell separation magnetic stand (Quad Technologies) for 5 minutes. The supernatant was then removed and replated. As shown, hydrogel complex-expanded cells were free of magnetic particles. The bottom panels of FIG. 17 show control bead-expanded T cells following an analogous separation process.

Other embodiments are in the claims.

What is claimed is:

1. A polymeric moiety comprising: a hydrogel of an alginic acid-polyethylene glycol (PEG) copolymer, a signal 1 stimulus configured to induce T cell expansion, and a cation; wherein the alginic acid-PEG copolymer changes from a solid matrix into a solution or suspension in response to a sufficient decrease of cationic concentration in the environment of the copolymer.

2. The polymeric moiety of claim 1, wherein the decrease in the cationic concentration in the environment of the polymer is caused by the presence of EDTA, EGTA, sodium citrate, BAPTA, crown ether, cryptand, phenanthroline sulfonate, dipyridyl sulfonate, dioxane, DME, diglyme, or triglyme.

3. The polymeric moiety of claim 1, wherein the cation is $Li^+$, $Mg^{2+}$, $Ca^{2+}$, $Sr^{2+}$, $Ba^{2+}$, $Zn^{2+}$, $Cu^{2+}$, or $Al^{3+}$.

4. The polymeric moiety of claim 1, wherein the hydrogel has an elastic modulus of less than 100,000 pascals (Pa).

5. The polymeric moiety of claim 1, wherein the hydrogel has at least one cross-sectional dimension of between about 50 nm and about 50 μm.

6. The polymeric moiety of claim 1, wherein the hydrogel is substantially spherical and has a diameter of between about 1 and 20 μm.

7. The polymeric moiety of claim 1, wherein the signal 1 stimulus is covalently attached to an alginic acid domain of the alginic acid-PEG copolymer.

8. The polymeric moiety of claim 1, further comprising a signal 2 stimulus.

9. The polymeric moiety of claim 8, wherein the molar ratio of the signal 1 stimulus and the signal 2 stimulus is between about 1:100 and about 100:1.

10. The polymeric moiety of claim 9, wherein the molar ratio of the signal 1 stimulus and the signal 2 stimulus is about 1:1.

11. The polymeric moiety of claim 1, wherein the signal 1 stimulus is antigen-specific.

12. The polymeric moiety of claim 1, wherein the signal 1 stimulus is an antibody or antigen-binding fragment thereof.

13. The polymeric moiety of claim 12, wherein the antibody or antigen binding fragment thereof is a monoclonal antibody or antigen-binding fragment thereof, a Fab, a humanized antibody or antigen-binding fragment thereof, a bispecific antibody or antigen-binding fragment thereof, a monovalent antibody or antigen-binding fragment thereof, a chimeric antibody or antigen-binding fragment thereof, a single-chain Fv molecule, a bispecific single chain Fv ((scFv') 2) molecule, a domain antibody, a diabody, a triabody, an affibody, a domain antibody, a SMIP, a nanobody, a Fv fragment, a Fab fragment, a F(ab') 2 molecule, or a tandem scFv (taFv) fragment.

14. The polymeric moiety of claim 12, wherein the signal 1 stimulus is anti CD3.

15. The polymeric moiety of claim 8, wherein the signal 1 stimulus is anti-CD3 and/or the signal 2 stimulus is anti-CD28.

16. The polymeric moiety of claim 1, wherein the signal 1 stimulus is covalently attached to the polymeric moiety.

17. The polymeric moiety of claim 1, wherein the hydrogel comprises an average of at least one signal 1 stimulus per square μm of surface area.

18. A polymeric moiety comprising: (i) a hydrogel of an alginic acid-PEG copolymer and $Ca^{2+}$, and (ii) anti-CD3 and anti-CD28; wherein the alginic acid-PEG copolymer changes from a solid matrix into a solution or suspension in response to a sufficient decrease of $Ca^{2+}$ concentration in the environment of the copolymer.

19. The polymeric moiety of claim 1, further comprising a separation unit, wherein the separation unit dissociates from the polymeric moiety upon the change of the alginic acid-PEG copolymer from the solid matrix into the solution or suspension.

20. The polymeric moiety of claim 19, wherein the separation unit is entrapped within the alginic acid-PEG copolymer.

21. The polymeric moiety of claim 19, wherein the separation unit comprises a magnetic material.

22. The polymeric moiety of claim 21, wherein the magnetic material is part of a nanoparticle or a microparticle.

23. The polymeric moiety of claim 18, further comprising a separation unit, wherein the separation unit dissociates from the polymeric moiety upon the change of the alginic acid-PEG copolymer from the solid matrix into the solution or suspension.

24. The polymeric moiety of claim 23, wherein the separation unit is entrapped within the alginic acid-PEG copolymer.

25. The polymeric moiety of claim 23, wherein the separation unit comprises a magnetic material.

26. The polymeric moiety of claim 25, wherein the magnetic material is part of a nanoparticle or a microparticle.

* * * * *